(12) United States Patent
Choe et al.

(10) Patent No.: US 11,814,374 B2
(45) Date of Patent: Nov. 14, 2023

(54) ORGANIC COMPOUND, AND ORGANIC LIGHT EMITTING DIODE AND ORGANIC LIGHT EMITTING DISPLAY DEVICE INCLUDING THE SAME

(71) Applicant: LG DISPLAY CO., LTD., Seoul (KR)

(72) Inventors: Ik-Rang Choe, Paju-si (KR);
Kyung-Jin Yoon, Paju-si (KR); In-Ae Shin, Paju-si (KR); Mi-Sang Yoo, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 403 days.

(21) Appl. No.: 16/932,007

(22) Filed: Jul. 17, 2020

(65) Prior Publication Data

US 2021/0024509 A1 Jan. 28, 2021

(30) Foreign Application Priority Data

Jul. 23, 2019 (KR) .......................... 10-2019-0088995

(51) Int. Cl.
*C07D 409/14* (2006.01)
*C07D 401/14* (2006.01)
(Continued)

(52) U.S. Cl.
CPC ......... *C07D 409/14* (2013.01); *C07D 401/14* (2013.01); *C07D 405/14* (2013.01);
(Continued)

(58) Field of Classification Search
CPC ............. H01L 51/0067; H01L 51/5012; H01L 51/0072; H10K 85/654; H10K 85/6572; H10K 50/11
See application file for complete search history.

(56) References Cited

U.S. PATENT DOCUMENTS 9,738,627 B2 8/2017 Low et al.
2017/0054082 A1 2/2017 Kim et al.
(Continued)

FOREIGN PATENT DOCUMENTS

CN 109564982 A 4/2019
EP 3418278 A1 12/2018
(Continued)

OTHER PUBLICATIONS

Wang et al, J. Mater. Chem. C, Mar. 13, 2019, 7, 4475-4483. (Year: 2019).*

(Continued)

*Primary Examiner* — Sean M DeGuire
(74) *Attorney, Agent, or Firm* — Morgan, Lewis & Bockius LLP

(57) ABSTRACT

The present disclosure provides an organic compound of following formula and an organic light emitting diode and an OLED device including the organic compound.

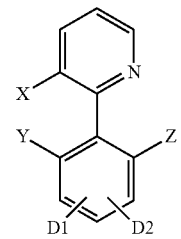

16 Claims, 4 Drawing Sheets

(51) Int. Cl.
*C07D 405/14* (2006.01)
*H10K 85/60* (2023.01)
*H10K 50/11* (2023.01)
*H10K 50/13* (2023.01)
*H10K 101/30* (2023.01)

(52) U.S. Cl.
CPC ....... *H10K 85/654* (2023.02); *H10K 85/6572* (2023.02); *H10K 85/6574* (2023.02); *H10K 50/11* (2023.02); *H10K 50/13* (2023.02); *H10K 2101/30* (2023.02)

(56) References Cited

U.S. PATENT DOCUMENTS

2018/0090705 A1* 3/2018 Jin .................. H01L 51/5012
2019/0214571 A1 7/2019 Huh et al.

FOREIGN PATENT DOCUMENTS

KR   10-2018-0010087 A    1/2018
WO   WO-2015022835 A1 *   2/2015 ........... C07D 401/14
WO   2016/089080 A1    6/2016

OTHER PUBLICATIONS

Graves, "Study of TADF Emitters in OLEDs", Durham theses, Durham University (2015) http://etheses.dur.acuk/11255/.
Extended European Search Report dated Feb. 19, 2021, issued in corresponding European Patent Application No. 20187481.5.
Office Action dated Dec. 30, 2022, issued in corresponding Chinese Patent Application No. 202010709110.0.

* cited by examiner

ORGANIC COMPOUND, AND ORGANIC LIGHT EMITTING DIODE AND ORGANIC LIGHT EMITTING DISPLAY DEVICE INCLUDING THE SAME

CROSS-REFERENCE TO RELATED APPLICATIONS

The present application claims the benefit of Korean Patent Application No. 10-2019-0088995 filed in the Republic of Korea on Jul. 23, 2019, which is hereby incorporated by reference in its entirety.

BACKGROUND

Field of Technology

The present disclosure relates to an organic compound, and more particularly, to an organic compound having high triplet energy and being used for an n-type host, and an organic light emitting diode and an organic light emitting display (OLED) device including the organic compound.

Discussion of the Related Art

Recently, requirement for flat panel display devices having small occupied area is increased. Among the flat panel display devices, a technology of an OLED device, which includes an organic light emitting diode and may be called to as an organic electroluminescent device, is rapidly developed.

The organic light emitting diode emits light by injecting electrons from a cathode as an electron injection electrode and holes from an anode as a hole injection electrode into an organic emitting layer, combining the electrons with the holes, generating an exciton, and transforming the exciton from an excited state to a ground state. A flexible transparent substrate, for example, a plastic substrate, can be used as a base substrate where elements are formed. In addition, the organic light emitting diode can be operated at a voltage (e.g., 10\T or below) lower than a voltage required to operate other display devices and has low power consumption. Moreover, the light from the organic light emitting diode has excellent color purity.

An emitting material layer of the organic emitting layer includes a host and a dopant. For example, an organic compound such as CBP may widely be used as the host of the emitting material layer.

However, in the related art organic light emitting diode, expected lifespan and emitting efficiency are not provided. Namely, there is a limitation in the lifespan and the emitting efficiency of the organic light emitting diode and the OLED device.

SUMMARY

The present disclosure is directed to an organic compound, an organic light emitting diode and an OLED device that substantially obviate one or more of the problems associated with the limitations and disadvantages of the related conventional art.

Additional features and advantages of the present disclosure are set forth in the description which follows, and will be apparent from the description, or evident by practice of the present disclosure. The objectives and other advantages of the present disclosure are realized and attained by the features described herein as well as in the appended drawings.

To achieve these and other advantages in accordance with the purpose of the embodiments of the present disclosure, as described herein, an aspect of the present disclosure comprises an organic compound of:

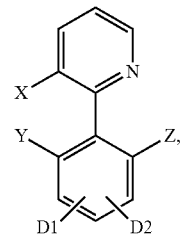

wherein each of X, Y, and Z is independently selected from hydrogen and a C1 to C20 alkyl group, and at least one of X, Y, and Z is selected from the C1 to C20 alkyl group, and wherein each of D1 and D2 is independently selected from a C10 to C60 heteroaryl group.

In another aspect, an organic light emitting diode comprises a first electrode; a second electrode facing the first electrode; and a first emitting material layer between the first and second electrodes and including an organic compound of:

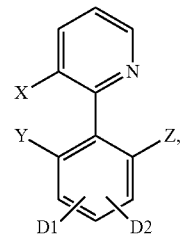

wherein each of X, Y, and Z is independently selected from hydrogen and a C1 to C20 alkyl group, and at least one of X, Y, and Z is selected from the C1 to C20 alkyl group, and wherein each of D1 and D2 is independently selected from a C10 to C60 heteroaryl group.

In another aspect, an organic light emitting display device comprises a substrate; an organic light emitting diode disposed on or over the substrate, the organic light emitting diode including: a first electrode; a second electrode facing the first electrode; and a first emitting material layer between the first and second electrodes; and a thin film transistor positioned between the substrate and the organic light emitting diode and connected to the organic light emitting diode, wherein the first emitting material layer includes an organic compound of:

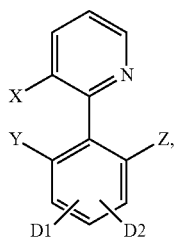

wherein each of X, Y, and Z is independently selected from hydrogen and a C1 to C20 alkyl group, and at least one of X, Y, and Z is selected from the C1 to C20 alkyl group, and wherein each of D1 and D2 is independently selected from a C10 to C60 heteroaryl group.

It is to be understood that both the foregoing general description and the following detailed description are exemplary and explanatory and are intended to further explain the present disclosure as claimed.

BRIEF DESCRIPTION OF THE DRAWINGS

The accompanying drawings, which are included to provide a further understanding of the present disclosure and are incorporated in and constitute a part of this specification, illustrate embodiments of the present disclosure and together with the description serve to explain principles of the present disclosure.

DETAILED DESCRIPTION

Reference will now be made in detail to some of the examples and preferred embodiments, which are illustrated in the accompanying drawings.

Figure 1:
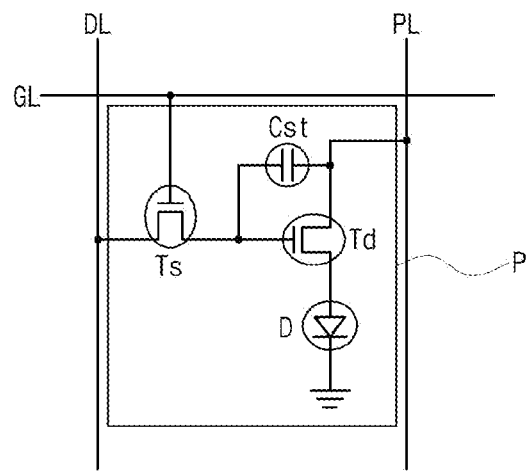
FIG. 1 is a schematic circuit diagram of an OLED device of the present disclosure.

FIG. 1 is a schematic circuit diagram of an OLED device of the present disclosure.

As shown in FIG. 1, an OLED device includes a gate line GL, a data line DL, a power line PL, a switching thin film transistor TFT Ts, a driving TFT Td, a storage capacitor Cst, and an organic light emitting diode D. The gate line GL and the data line DL cross each other to define a pixel region SP.

The switching TFT Ts is connected to the gate line GL and the data line DL, and the driving TFT Td and the storage capacitor Cst are connected to the switching TFT Ts and the power line PL. The organic light emitting diode D is connected to the driving TFT Td.

In the OLED device, when the switching TFT Ts is turned on by a gate signal applied through the gate line GL, a data signal from the data line DL is applied to the gate electrode of the driving TFT Td and an electrode of the storage capacitor Cst.

When the driving TFT Td is turned on by the data signal, an electric current is supplied to the organic light emitting diode D from the power line PL. As a result, the organic light emitting diode D emits light. In this case, when the driving TFT Td is turned on, a level of an electric current applied from the power line PL to the organic light emitting diode D is determined such that the organic light emitting diode D can produce a gray scale.

The storage capacitor Cst serves to maintain the voltage of the gate electrode of the driving TFT Td when the switching TFT Ts is turned off. Accordingly, even if the switching TFT Ts is turned off, a level of an electric current applied from the power line PL to the organic light emitting diode D is maintained to next frame.

As a result, the OLED device displays a desired image.

Figure 2:
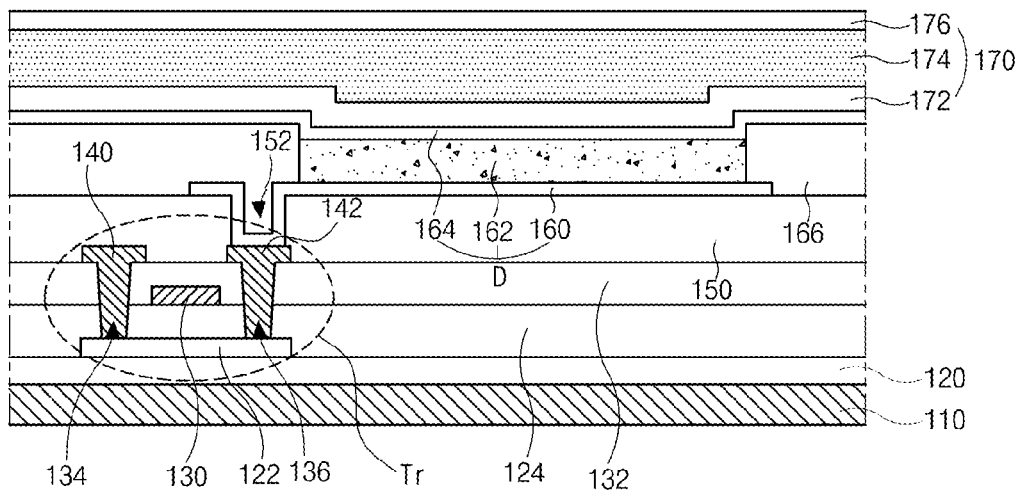
FIG. 2 is a schematic cross-sectional view of an OLED device of the present disclosure.

FIG. 2 is a schematic cross-sectional view of an OLED device of the present disclosure.

As shown in FIG. 2, the OLED device 100 includes a substrate 110, a TFT Tr and an organic light emitting diode D connected to the TFT Tr.

The substrate 110 may be a glass substrate or a plastic substrate. For example, the substrate 110 may be a polyimide substrate.

A buffer layer 120 is formed on the substrate, and the TFT Tr is formed on the buffer layer 120. The buffer layer 120 may be omitted.

A semiconductor layer 122 is formed on the buffer layer 120. The semiconductor layer 122 may include an oxide semiconductor material or polycrystalline silicon.

When the semiconductor layer 122 includes the oxide semiconductor material, a light-shielding pattern (not shown) may be formed under the semiconductor layer 122. The light to the semiconductor layer 122 is shielded or blocked by the light-shielding pattern such that thermal degradation of the semiconductor layer 122 can be prevented. On the other hand, when the semiconductor layer 122 includes polycrystalline silicon, impurities may be doped into both sides of the semiconductor layer 122.

A gate insulating layer 124 is formed on the semiconductor layer 122. The gate insulating layer 124 may be formed of an inorganic insulating material such as silicon oxide or silicon nitride.

A gate electrode 130, which is formed of a conductive material, e.g., metal, is formed on the gate insulating layer 124 to correspond to a center of the semiconductor layer 122.

In FIG. 2, the gate insulating layer 124 is formed on an entire surface of the substrate 110. Alternatively, the gate insulating layer 124 may be patterned to have the same shape as the gate electrode 130.

An interlayer insulating layer 132, which is formed of an insulating material, is formed on the gate electrode 130. The interlayer insulating layer 132 may be formed of an inorganic insulating material, e.g., silicon oxide or silicon nitride, or an organic insulating material, e.g., benzocyclobutene or photo-acryl.

The interlayer insulating layer 132 includes first and second contact holes 134 and 136 exposing both sides of the semiconductor layer 122. The first and second contact holes 134 and 136 are positioned at both sides of the gate electrode 130 to be spaced apart from the gate electrode 130.

The first and second contact holes 134 and 136 are formed through the gate insulating layer 124. Alternatively, when the gate insulating layer 124 is patterned to have the same shape as the gate electrode 130, the first and second contact holes 134 and 136 is formed only through the interlayer insulating layer 132.

A source electrode 140 and a drain electrode 142, which are formed of a conductive material, e.g., metal, are formed on the interlayer insulating layer 132.

The source electrode 140 and the drain electrode 142 are spaced apart from each other with respect to the gate electrode 130 and respectively contact both sides of the semiconductor layer 122 through the first and second contact holes 134 and 136.

The semiconductor layer 122, the gate electrode 130, the source electrode 140 and the drain electrode 142 constitute the TFT Tr. The TFT Tr serves as a driving element.

In the TFT Tr, the gate electrode 130, the source electrode 140, and the drain electrode 142 are positioned over the semiconductor layer 122. Namely, the TFT Tr has a coplanar structure.

Alternatively, in the TFT Tr, the gate electrode may be positioned under the semiconductor layer, and the source and drain electrodes may be positioned over the semiconductor layer such that the TFT Tr may have an inverted staggered structure. In this instance, the semiconductor layer may include amorphous silicon.

Although not shown, the gate line and the data line cross each other to define the pixel region, and the switching TFT is formed to be connected to the gate and data lines. The switching TFT is connected to the TFT Tr as the driving element.

In addition, the power line, which may be formed to be parallel to and spaced apart from one of the gate and data lines, and the storage capacitor for maintaining the voltage of the gate electrode of the TFT Tr in one frame may be further formed.

A passivation layer 150, which includes a drain contact hole 152 exposing the drain electrode 142 of the TFT Tr, is formed to cover the TFT Tr.

A first electrode 160, which is connected to the drain electrode 142 of the TFT Tr through the drain contact hole 152, is separately formed in each pixel region. The first electrode 160 may be an anode and may be formed of a conductive material having a relatively high work function. For example, the first electrode 160 may be formed of a transparent conductive material such as indium-tin-oxide (ITO) or indium-zinc-oxide (IZO).

When the OLED device 100 is operated in a top-emission type, a reflection electrode or a reflection layer may be formed under the first electrode 160. For example, the reflection electrode or the reflection layer may be formed of aluminum-palladium-copper (APC) alloy.

A bank layer 166 is formed on the passivation layer 150 to cover an edge of the first electrode 160. Namely, the bank layer 166 is positioned at a boundary of the pixel region and exposes a center of the first electrode 160 in the pixel region.

An organic emitting layer 162 is formed on the first electrode 160. The organic emitting layer 162 may have a single-layered structure of an emitting material layer including an emitting material. To increase an emitting efficiency of the OLED device, the organic emitting layer 162 may have a multi-layered structure.

A second electrode 164 is formed over the substrate 110 where the organic emitting layer 162 is formed. The second electrode 164 covers an entire surface of the display area and may be formed of a conductive material having a relatively low work function to serve as a cathode. For example, the second electrode 164 may be formed of aluminum (Al), magnesium (Mg) or Al—Mg alloy.

The first electrode 160, the organic emitting layer 162 and the second electrode 164 constitute the organic light emitting diode D.

An encapsulation film 170 is formed on the second electrode 164 to prevent penetration of moisture into the organic light emitting diode D. The encapsulation film 170 includes a first inorganic insulating layer 172, an organic insulating layer 174 and a second inorganic insulating layer 176 sequentially stacked, but it is not limited thereto.

A polarization plate (not shown) for reducing an ambient light reflection may be disposed over the top-emission type organic light emitting diode D. For example, the polarization plate may be a circular polarization plate.

In addition, a cover window (not shown) may be attached to the encapsulation film 170 or the polarization plate. In this instance, the substrate 110 and the cover window have a flexible property such that a flexible OLED device may be provided.

Figure 3:
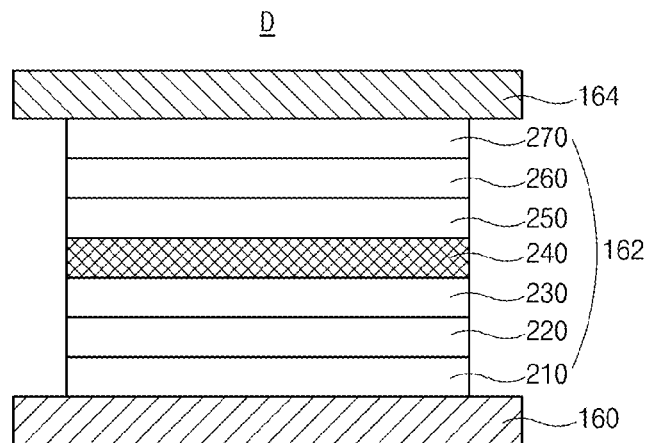
FIG. 3 is a schematic cross-sectional view of an organic light emitting diode of the present disclosure.

FIG. 3 is a schematic cross-sectional view of an organic light emitting diode of the present disclosure.

As shown in FIG. 3, the organic light emitting diode D includes the first and second electrodes 160 and 164, which face each other, and the organic emitting layer 162 therebetween. The organic emitting layer 162 includes an emitting material layer (EML) 240 between the first and second electrodes 160 and 164, a hole transporting layer (HTL) 220 between the first electrode 160 and the EML 240 and an electron transporting layer (ETL) 260 between the second electrode 164 and the EML 240.

In addition, the organic emitting layer 162 may further include a hole injection layer (HIL) 210 between the first electrode 160 and the HTL 220 and an electron injection layer (EIL) 270 between the second electrode 164 and the ETL 260.

Moreover, the organic emitting layer 162 may further include an electron blocking layer (EBL) 230 between the HTL 220 and the EML 240 and a hole blocking layer (HBL) 250 between the EML 240 and the ETL 260.

The organic emitting layer 162, preferably the EML 240 includes an organic compound of Formula 1 as a host and further includes a dopant.

[Formula 1]

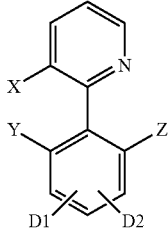

In Formula 1, each of X, Y, and Z is independently selected from hydrogen and a C1 to C20 alkyl group, and at least one of X, Y, and Z is selected from a C1 to C20 alkyl group. It is preferable that one or two of X, Y and Z may be a C1 to C10 alkyl group.

For example, at least one of X, Y and Z may be selected from the group consisting of methyl, ethyl, propyl (isopropyl) and butyl (t-butyl). It is preferable that at least one of X, Y and Z may be methyl.

In addition, each of D1 and D2 is independently selected from a C10 to C60 heteroaryl group. D1 and D2 are same or different. The heteroaryl includes substituted or non-substituted heteroaryl. For example, each of D1 and D2 may be selected from the group consisting of substituted or non-substituted carbazolyl, substituted or non-substituted dibenzofuranyl and substituted or non-substituted dibenzothiophenyl. In this instance, the substituent may be carbazole group or cyano group.

For example, D1 and D2 may be combined the phenyl moiety at a meta-position and may be selected from Formula 2.

[Formula 2]

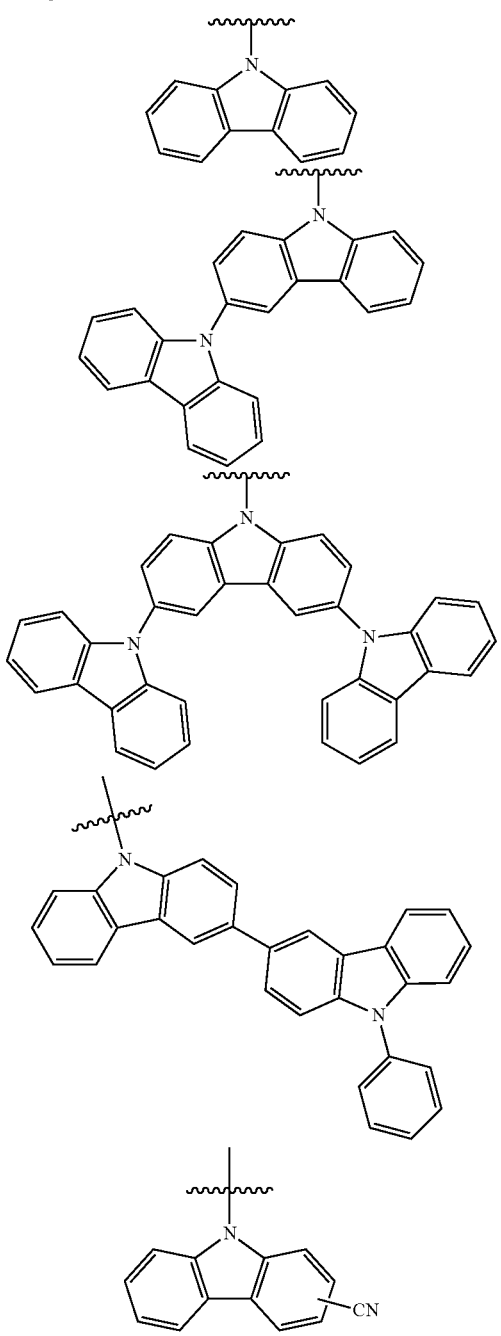

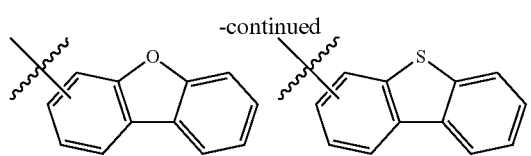

Namely, in the organic compound of the present disclosure, an electron acceptor moiety, which is a substituted or non-substituted pyridyl group, and an electron donor moiety, which is a substituted or non-substituted C10 to C60 heteroaryl group, are combined (connected) to a substituted or non-substituted phenylene linker. In other words, the organic compound of the present disclosure includes two electron donor moieties and thus has n-type properties. In addition, since the electron acceptor moiety and/or the linker is substituted by a C1 to C10 alkyl group, the decrease of the triplet energy of the organic compound by the n-type property is prevented. Moreover, the organic compound of the present disclosure has a bipolar characteristic, thereby improving the charge balance in the EML. As a result, the emitting efficiency of the organic light emitting diode and the OLED device is improved.

Accordingly, the organic compound of the present disclosure has the n-type property and high triplet energy.

The organic compound of the present disclosure may be used as an n-type host. As described above, the organic compound of the present disclosure has high triplet energy, the organic light emitting diode and the OLED device including the organic compound as the host in the EML have advantages in the emitting efficiency and the lifespan.

In the EML 240, the quenching problem of the exciton by an interaction between the triplet exciton of the dopant and the hole-polaron may be generated. To prevent the quenching problem, n-type host is required. However, when the n-type property of the host is increased, the triplet energy of the host is decreased such that the triplet exciton of the dopant is transited into the triplet energy level of the host. As a result, the emitting efficiency is decreased.

However, in the organic compound of the present disclosure since the electron acceptor moiety, which is a substituted or non-substituted pyridyl group, and the electron donor moiety, which is a substituted or non-substituted C10 to C60 heteroaryl group, are combined (connected) to a substituted or non-substituted phenylene linker and the electron acceptor moiety and/or the linker is substituted by a C1 to C10 alkyl group, the organic compound has high triplet energy.

Accordingly, in the organic light emitting diode D of the present disclosure, the quenching problem of the exciton by an interaction between the triplet exciton of the dopant and the hole-polaron and the energy transiting problem from the dopant to the host by low triplet energy of the host are prevented or minimized.

In addition, when the organic compound of the present disclosure is used as the n-type host, the emitting zone, i.e., a recombination zone, resulting from the combination between the hole and the electron is generated at a region near an interface between the EML and the EBL such that the lifespan of the organic light emitting diode is improved.

Figure 4A:
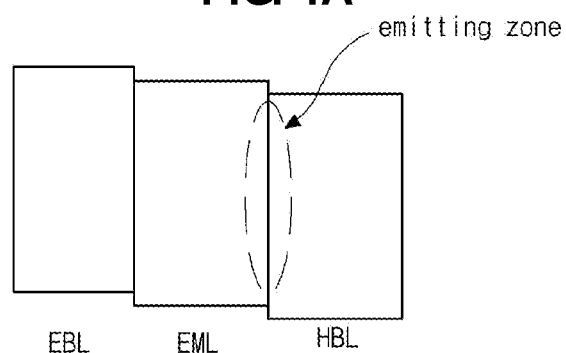
FIGS. 4A and 4B are schematic view illustrating emission in an organic light emitting diode using a p-type host and an organic light emitting diode of the present disclosure, respectively.

Namely, referring to FIG. 4A, which is a view illustrating emission in an organic light emitting diode using a p-type host, the mobility of the hole becomes relatively fast due to the p-type host in the EML such that the emitting zone (recombination zone) is generated to be near an interface between the EML and the HBL.

Figure 4B:
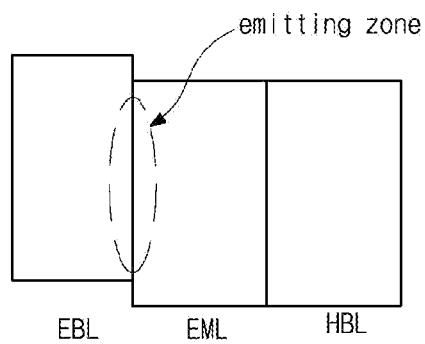

On the other hand, referring to FIG. 4B, which is a view illustrating emission in an organic light emitting diode of the present disclosure, the mobility of the electron becomes relatively fast due to the n-type host, i.e., the organic compound of the present disclosure, in the EML such that the emitting zone (recombination zone) is generated to be near an interface between the EML and the EBL.

A position of the emitting zone is shifted by the property difference between the p-type host and the n-type host such that the lifespan of the organic light emitting diode (D) is also changed.

In all cases of the light emitting diodes using the p-type host and the n-type host, the emitting zone is generated to be shifted one side of the EML. However, when the emitting zone is generated to be closer to the first electrode, for example, in a region near an interface between one of the EBL and the HTL and the EML, the emitting efficiency and the lifespan of the organic light emitting diode are improved.

The dopant used to the EML 240 with the organic compound of the present disclosure as the host may be at least one of a fluorescent compound (fluorescent dopant), a phosphorescent compound (phosphorescent dopant) and a delayed fluorescent compound (delayed fluorescent dopant). The dopant may have a weight ratio, i.e., wt %, of about 1 to 50 with respect to the host.

Figure 5:
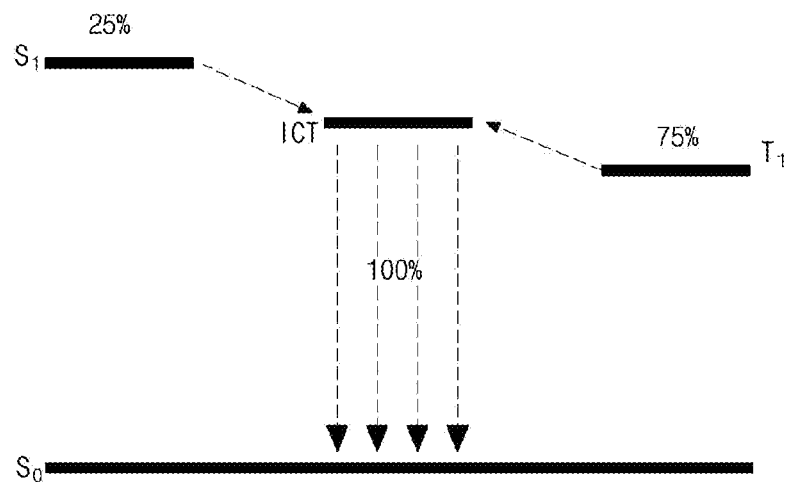
FIG. 5 is a view illustrating an emission mechanism of a delayed fluorescent compound.

For example, referring to FIG. 5, which is a view illustrating an emission mechanism of a delayed fluorescent compound, in the delayed fluorescent compound, the singlet exciton and the triplet exciton are engaged in the emission such that the quantum efficiency is improved.

Namely, in the delayed florescent compound, when the triplet exciton is activated by a field or heat, and the triplet exciton and the singlet exciton are transferred into an intermediated state and transited into a ground state to emit light. In other words, the singlet state and the triplet state are engaged in the emission such that the emitting efficiency is improved.

When the EML 240 includes the delayed fluorescent dopant (delayed fluorescent compound) with the organic compound of the present disclosure as the host, a difference between the HOMO of the host "$HOMO_{Host}$" and the HOMO of the delayed fluorescent dopant "$HOMO_{Dopant}$" or a difference between the LUMO of the host "$LUMO_{Host}$" and the LUMO of the delayed fluorescent dopant "$LUMO_{Dopant}$" is less than about 0.5 eV. In this instance, the charge transfer efficiency from the host to the dopant may be improved.

The triplet energy of the delayed fluorescent dopant is smaller than the triplet energy of the host, and a difference between the singlet energy of the delayed fluorescent dopant and the triplet energy of the delayed fluorescent dopant is less than 0.3 eV. ($\Delta E_{ST} \geq 0.3$ eV.) As the difference "$\Delta E_{ST}$" is smaller, the emitting efficiency is higher. In addition, even if the difference "$\Delta E_{ST}$" between the singlet energy of the delayed fluorescent dopant and the triplet energy of the delayed fluorescent dopant is about 0.3 eV, which is relatively large, the excitons in the singlet state and the excitons in the triplet state can be transited into the intermediate state.

The EML 240 may include the organic compound of the present disclosure as the host with the delayed fluorescent dopant as a first dopant and the fluorescent dopant as a second dopant. The summation of the first dopant and the second dopant may be about 1 to 50 wt % with respect to the host.

The singlet energy of the first dopant may be smaller than that of the host and larger than that of the second dopant. The triplet energy of the first dopant may be smaller than that of the host and larger than that of the second dopant.

Figure 6:
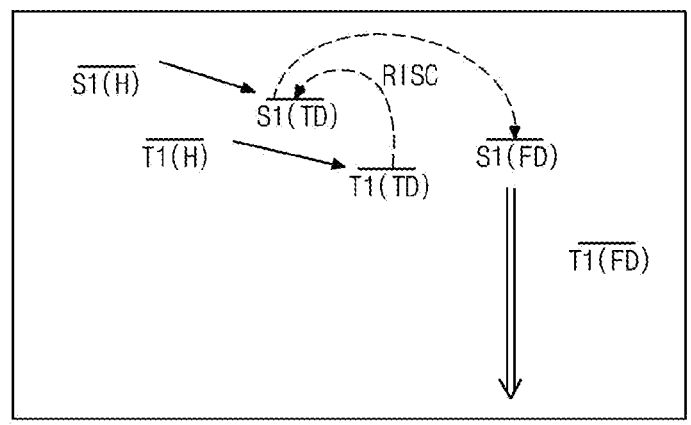
FIG. 6 is a view illustrating an emission mechanism of an organic light emitting diode of the present disclosure.

Referring to FIG. 6, which is a view illustrating an emission mechanism of an organic light emitting diode of the present disclosure, the triplet energy ($E_{T1}(TD)$) of the delayed fluorescent dopant, i.e., the first dopant, is converted into the singlet energy ($E_{s1}(TD)$) by an effect of a reverse intersystem crossing (RISC), and the singlet energy ($E_{s1}(TD)$) of the delayed fluorescent dopant is transferred into the singlet energy ($E_{s1}(FD)$) of the fluorescent dopant, i.e., the second dopant by an effect of Foster resonance energy transfer. As a result, the light is emitted from the fluorescent dopant.

In the organic light emitting diode D, since the EML 240 includes the host, the first dopant and the second dopant, the emitting efficiency and the color purity are improved. Namely, since the energy is transferred from the host into the first dopant and both the singlet energy and the triplet energy of the first dopant are transferred into the second dopant, the emission is generated from the second dopant such that the quantum efficiency of the organic light emitting diode D is increased and the full width at half maximum (FWHM) of the light from the organic light emitting diode D is narrowed.

The delayed fluorescent dopant as the first dopant has high quantum efficiency. However, since the light emitted from the delayed fluorescent dopant has wide FWHM, the light from the delayed fluorescent dopant has bad color purity. On the other hand, the fluorescent dopant as the second dopant has narrow FWHM and high color purity. However, since the triplet energy of the fluorescent dopant is not engaged in the emission, the fluorescent dopant has low quantum efficiency.

Since the EML 240 of the organic light emitting diode D in the present disclosure includes the host, the first dopant and the second dopant, the organic light emitting diode D has advantages in both the emitting efficiency and the color purity.

In addition, since the organic compound of the present disclosure, which has high triplet energy and the n-type property, is used as the host, the emitting efficiency is further improved.

For example, the organic compound of the present disclosure in Formula 1 may be one of compounds in Formula 3.

[Formula 3]

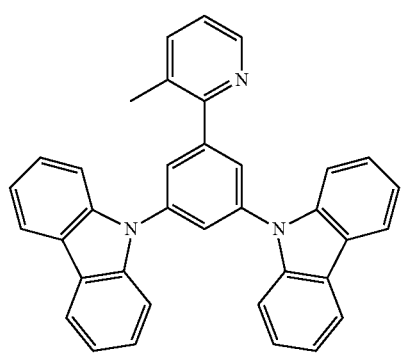

1-1

1-2
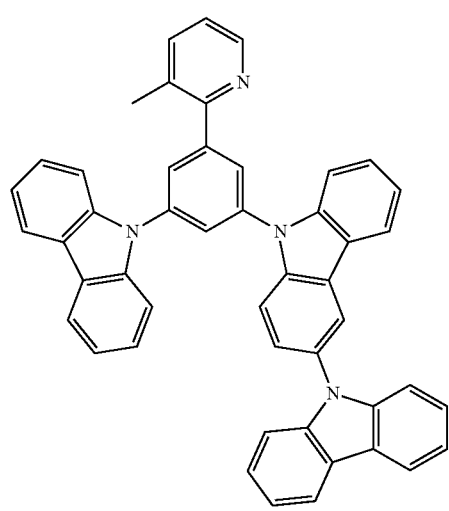
1-5
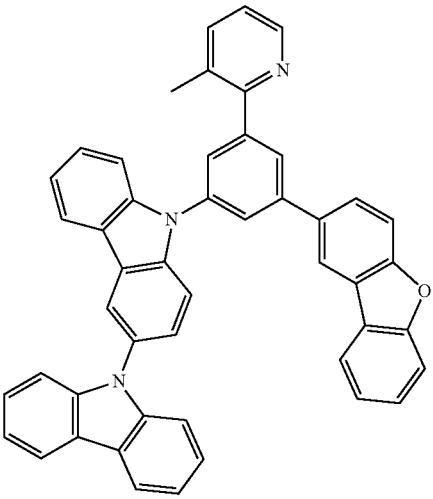
1-3
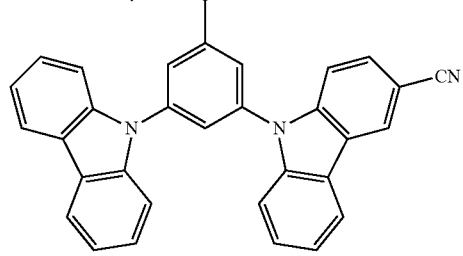
1-6
1-4
1-7
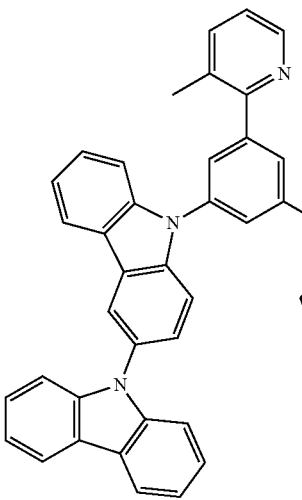

1-8
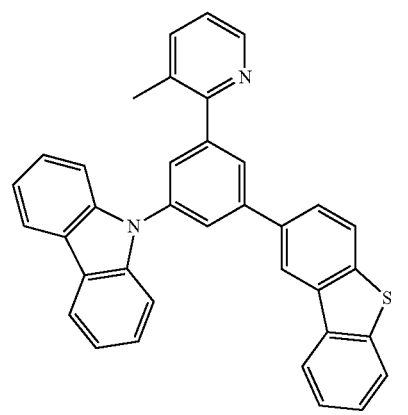
1-9
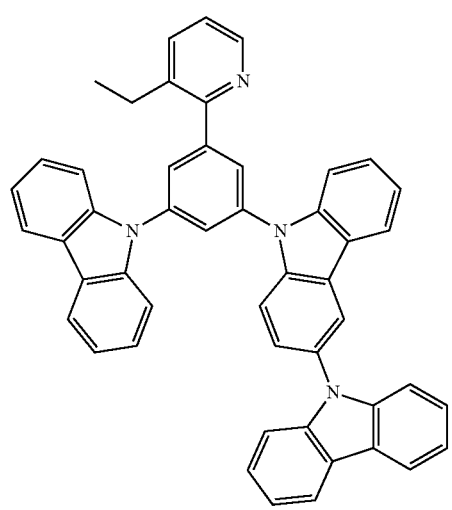
1-10
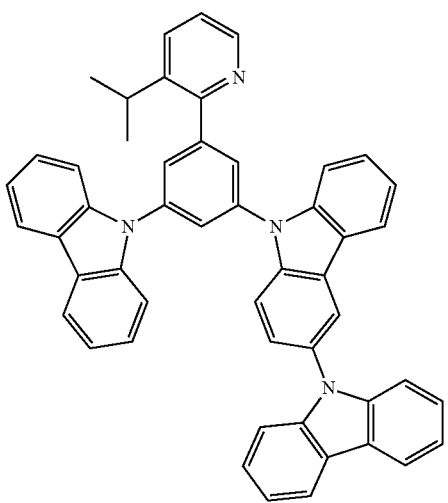
1-11
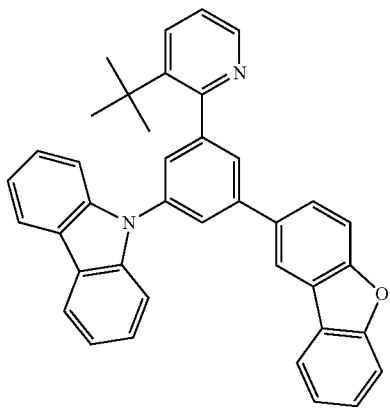
1-12
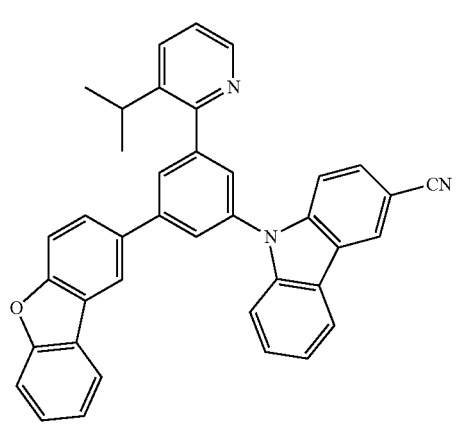
1-13
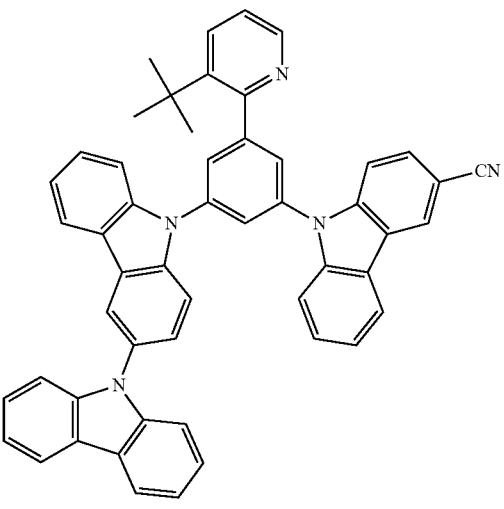

1-14
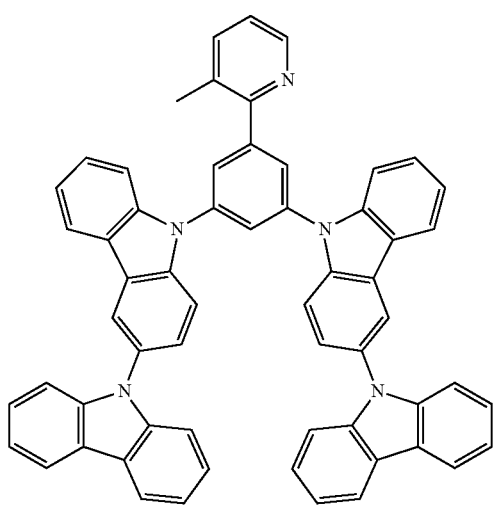
2-1
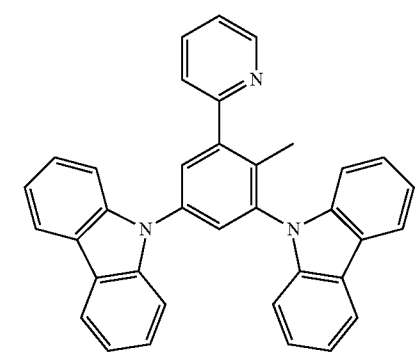
2-2
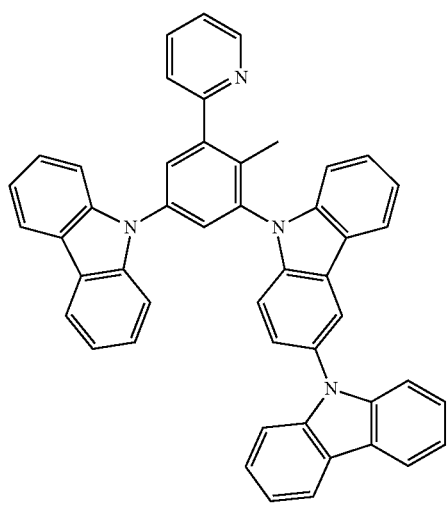
2-3
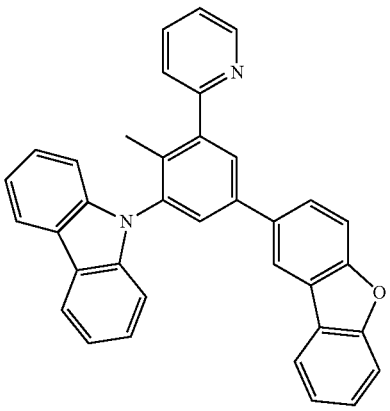
2-4
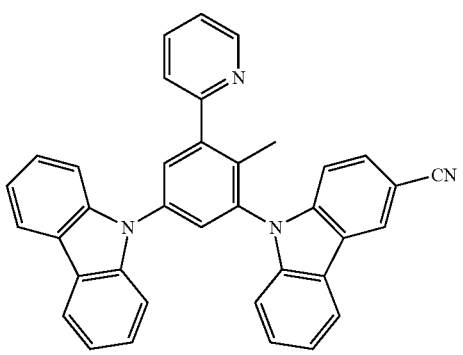
2-5
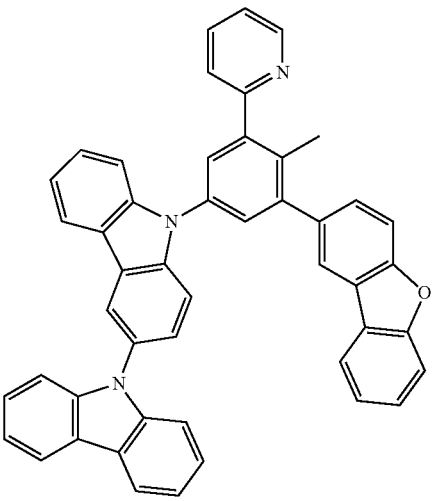

2-6
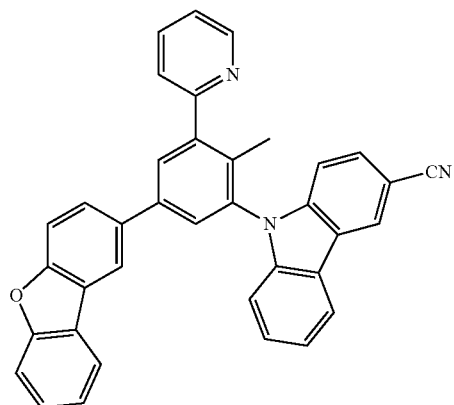
2-7
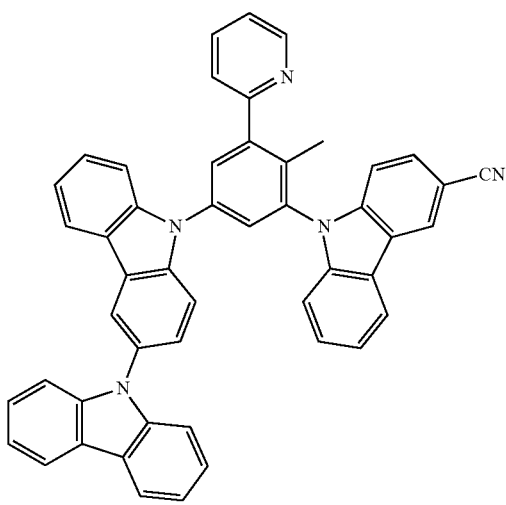
2-8
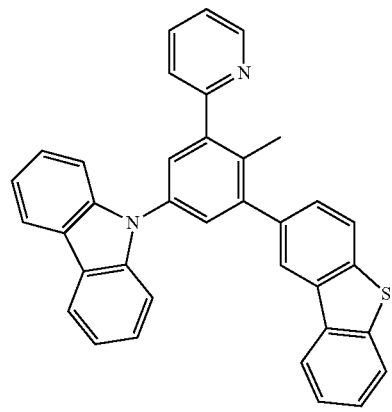
2-9
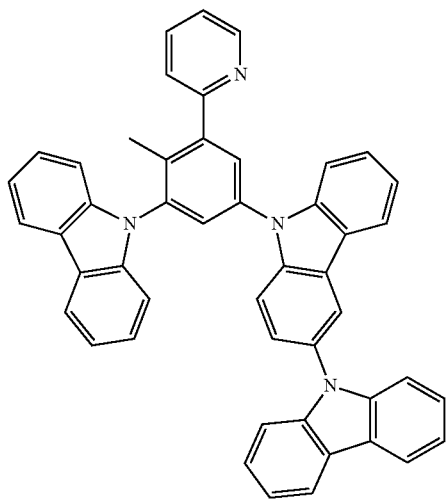
2-10
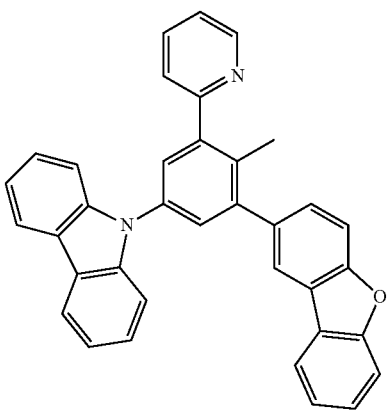
2-11
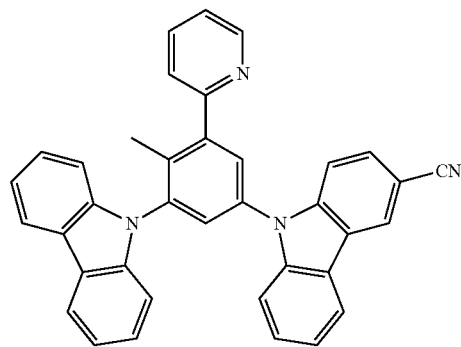

2-12
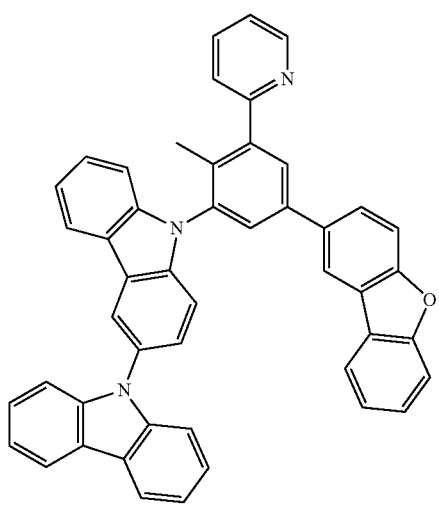
2-13
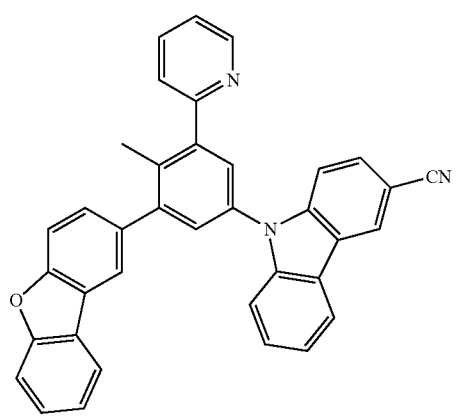
2-14
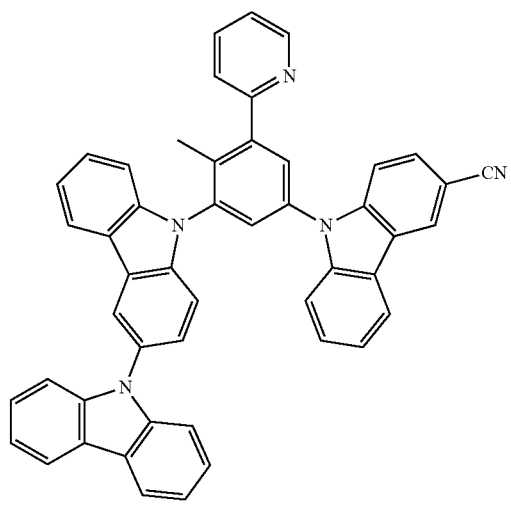
2-15
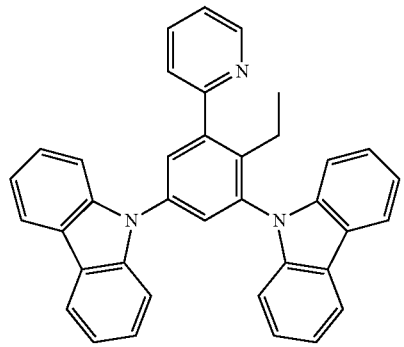
2-16
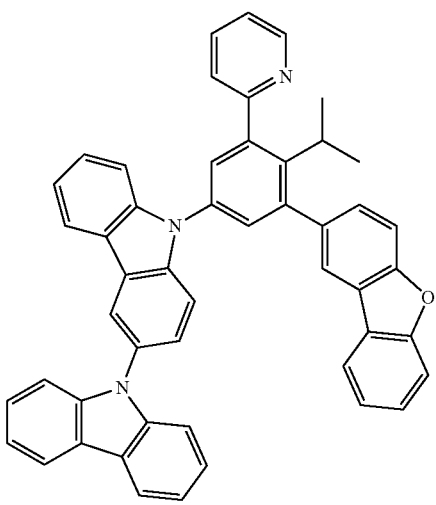
2-17
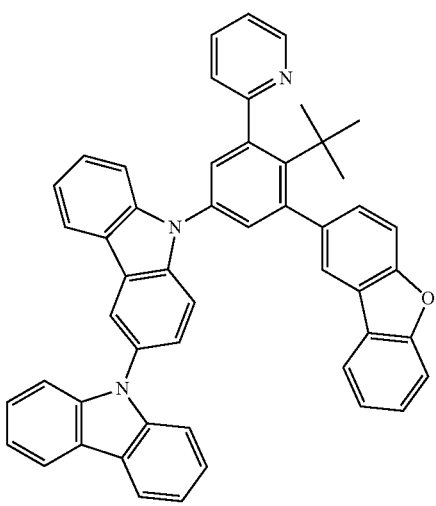

2-18
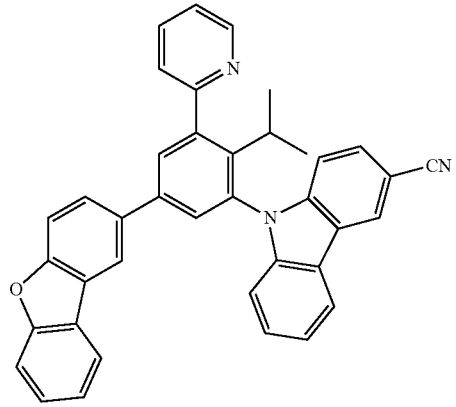
2-21
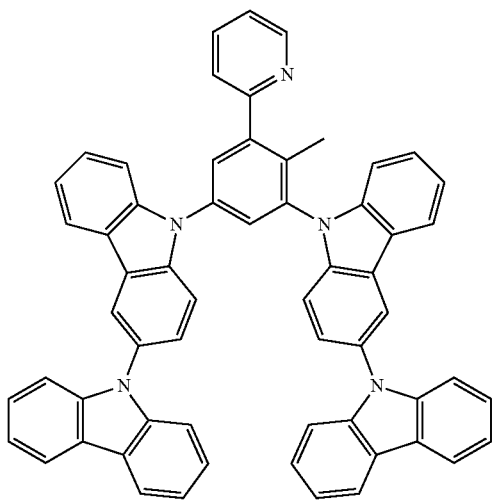
2-19
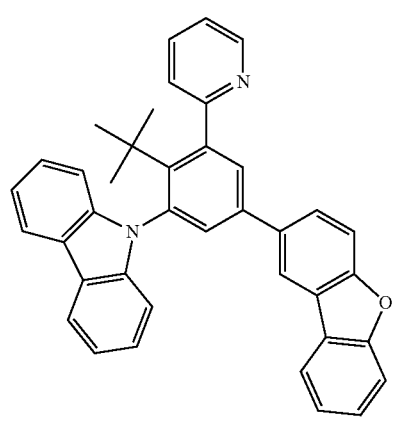
3-1
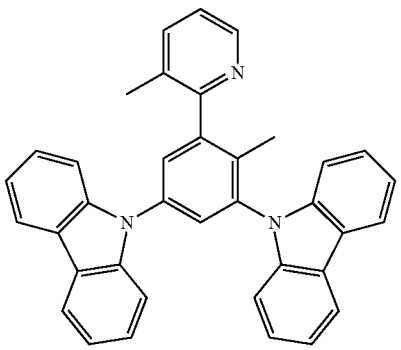
2-20
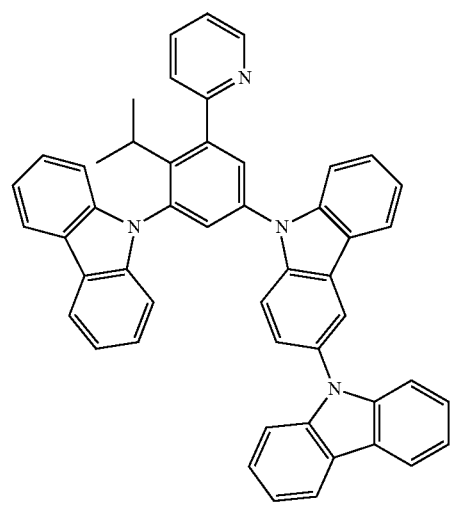
3-2
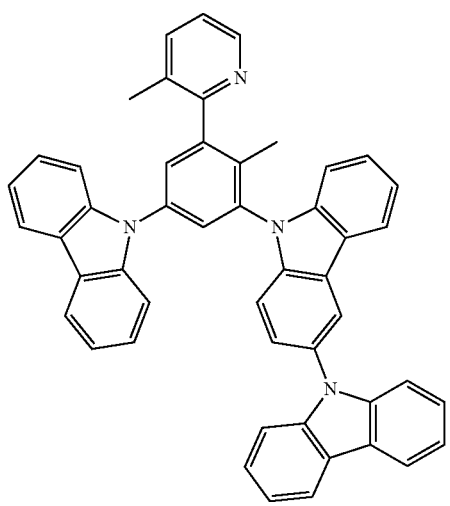

3-3
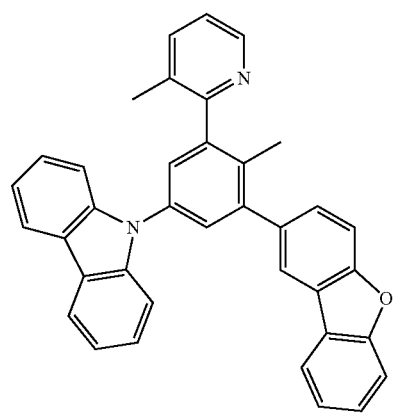
3-4
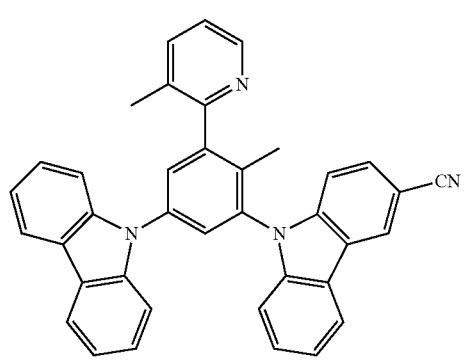
3-5
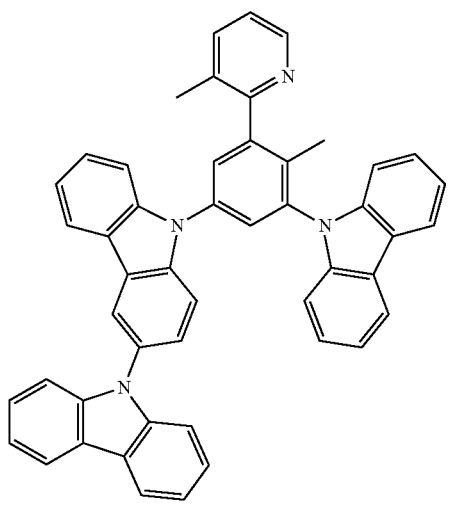
3-6
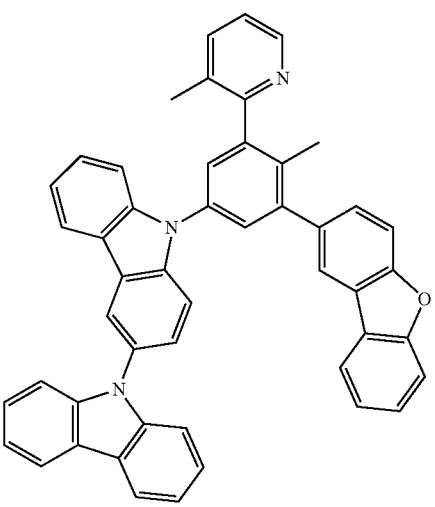
3-7
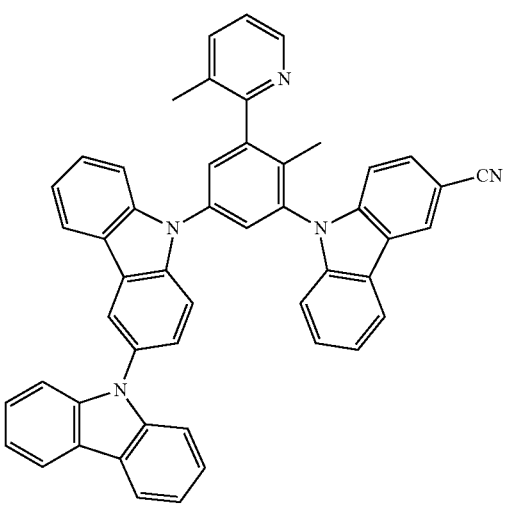
3-8
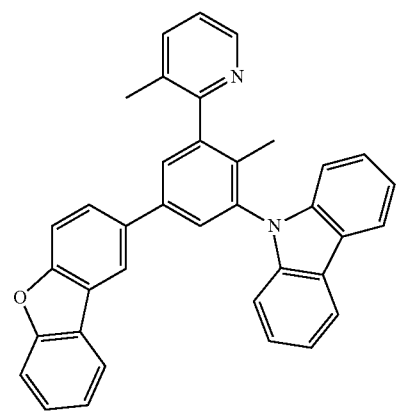

25
-continued
3-9
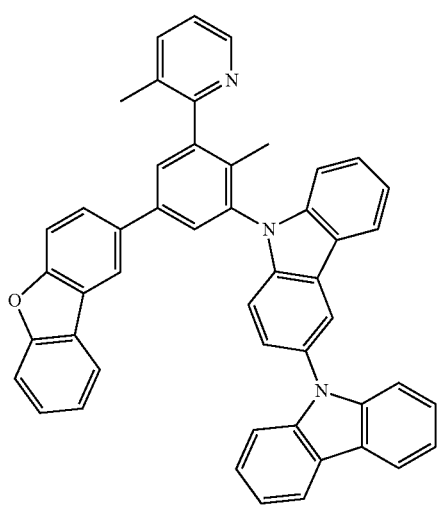
3-10
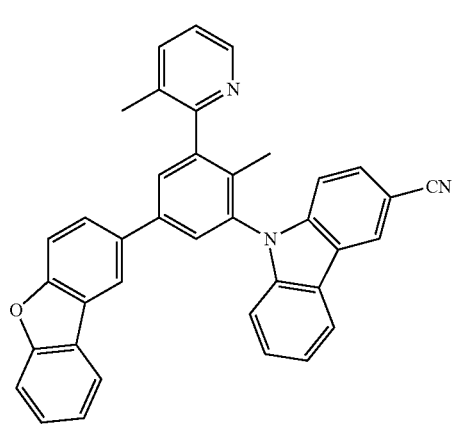
3-11
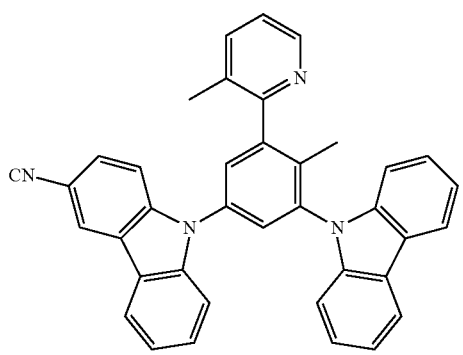
26
-continued
3-12
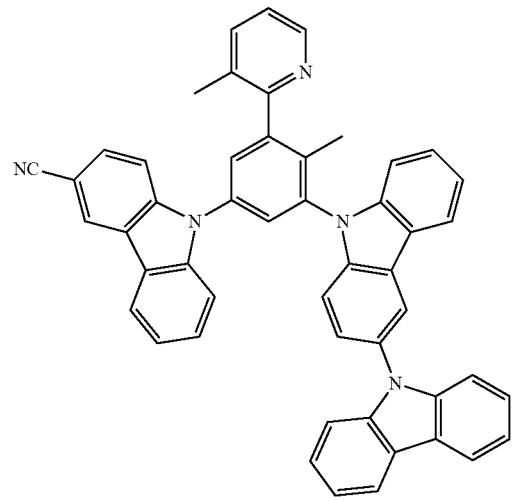
3-13
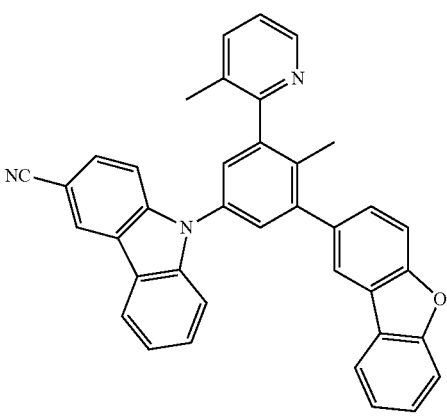
3-14
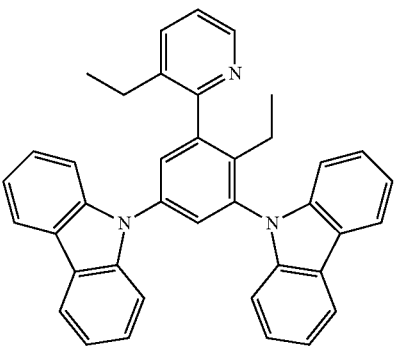

3-15
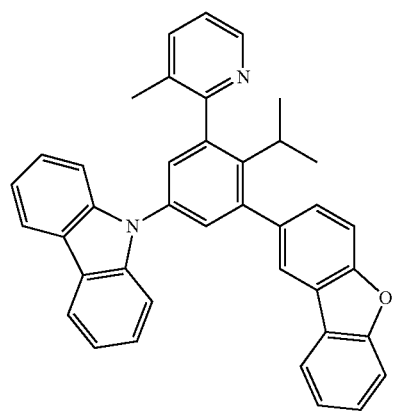
3-16
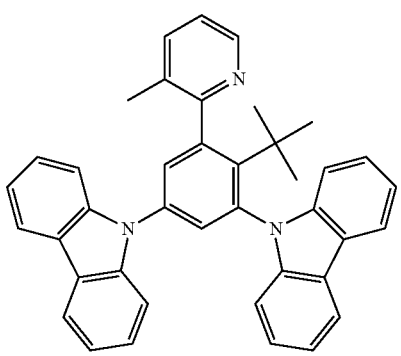
3-17
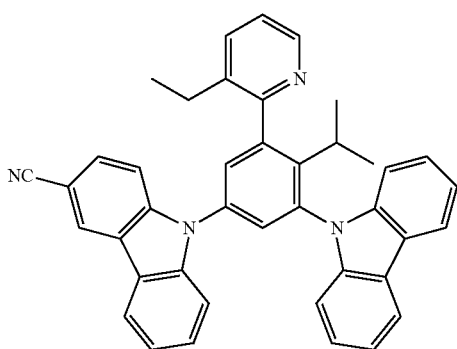
3-18
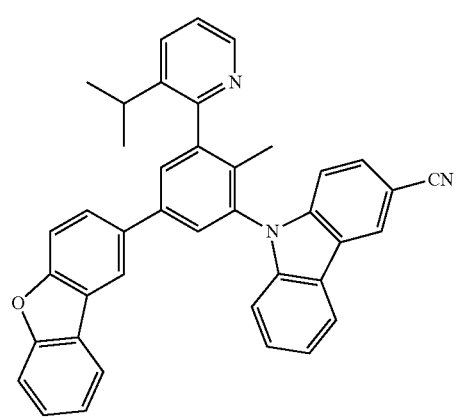
3-19
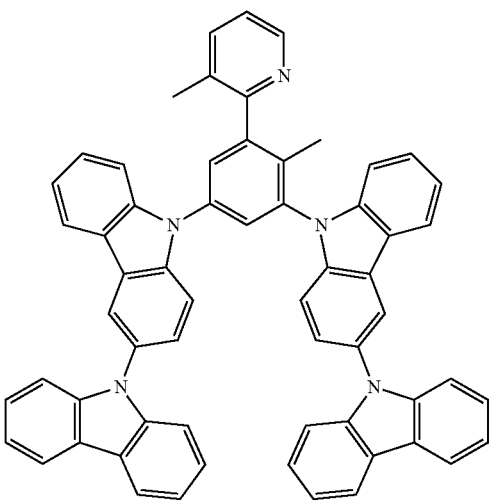
4-1
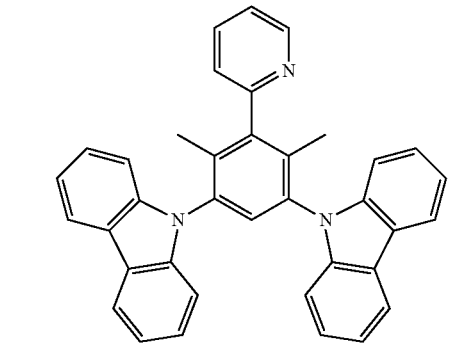
4-2
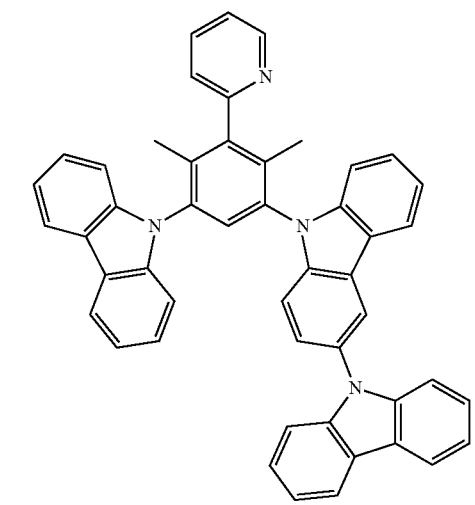

4-3
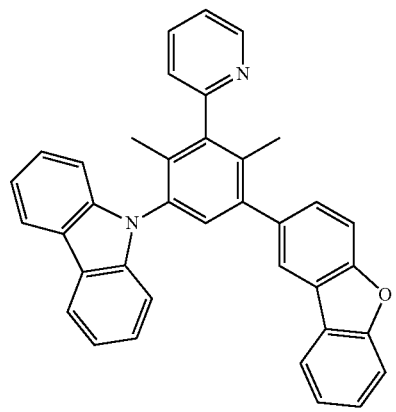
4-4
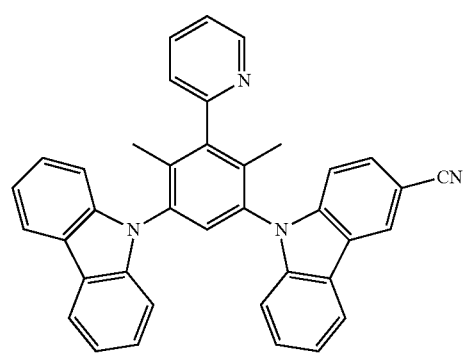
4-5
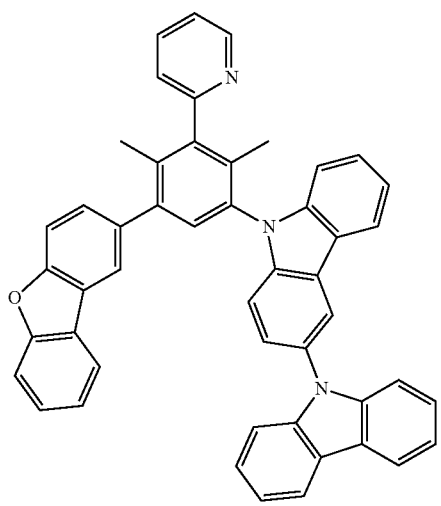
4-6
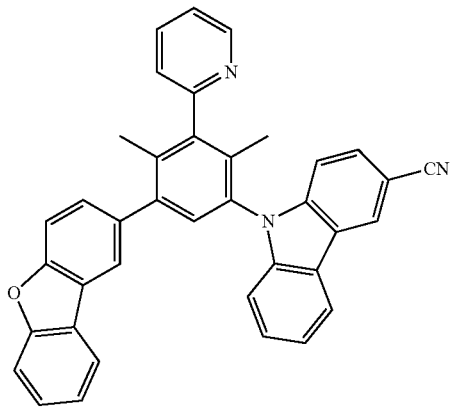
4-7
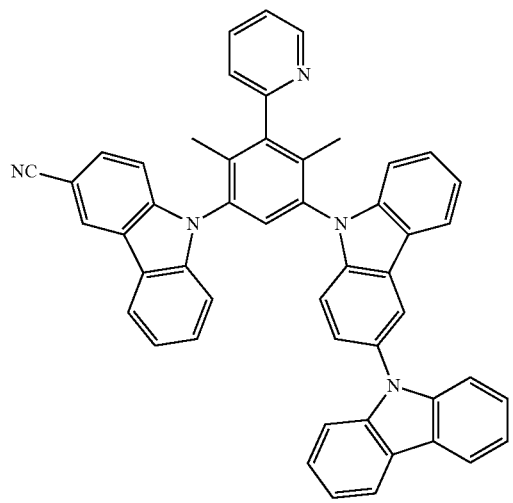
4-8
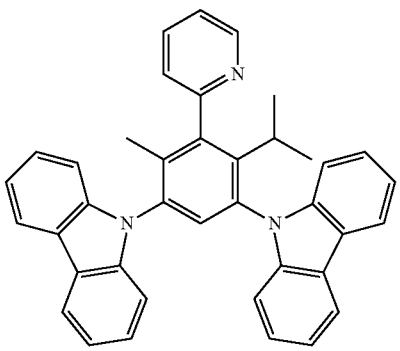

4-9
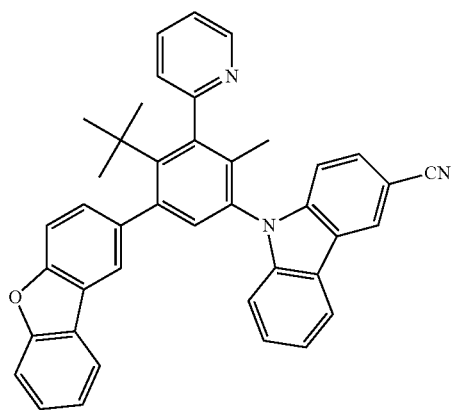
4-12
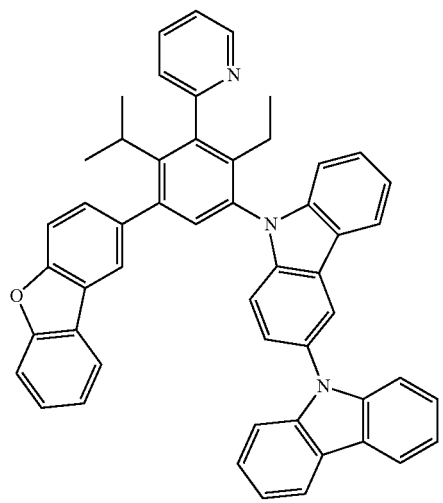
4-10
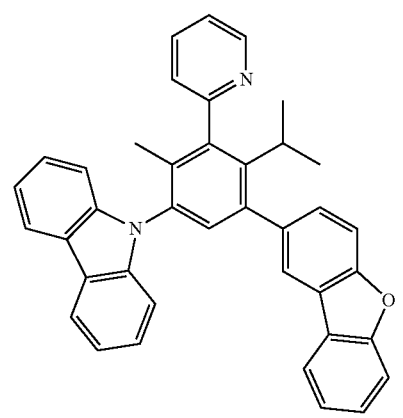
4-13
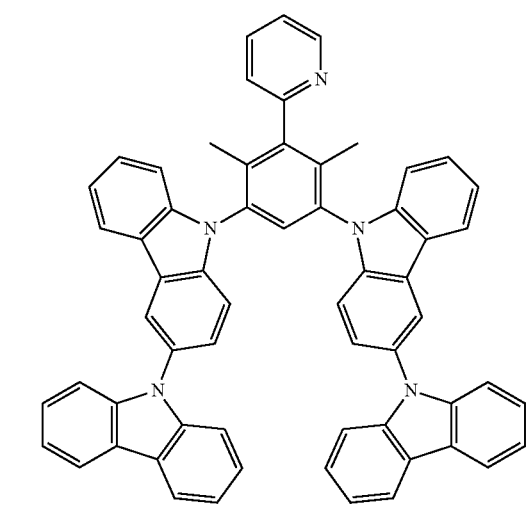
4-11
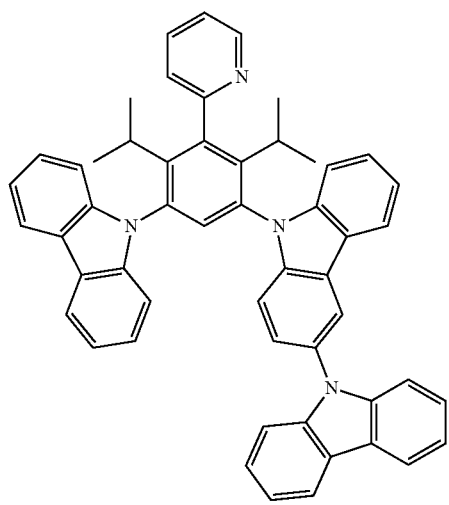
[Synthesis of Organic Compounds]
1. Synthesis of Compound 1-2
(1) Compound C
[Reaction Formula 1-1]
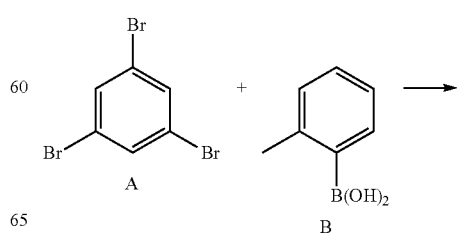

-continued

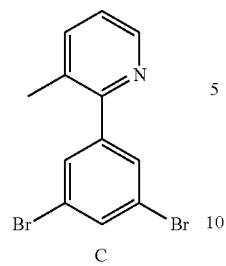

C

Under nitrogen condition, the compound A was dissolved in a mixed solution of tetrahydrofuran and toluene (volume ratio=5:1), and the compound B (0.9 equivalent) was added. Potassium carbonate (4.0 equivalent) was dissolved in the DI water, and Pd(0) (0.04 equivalent) were added. The reaction mixture was refluxed and stirred under the temperature of 80° C. for 8 hrs, and then the reaction was finished. The resultant was extracted using an organic solvent, and the organic solvent was removed. The resultant was columned and reprecipitated such that the compound C was obtained.

(2) Compound E

[Reaction Formula 1-2]

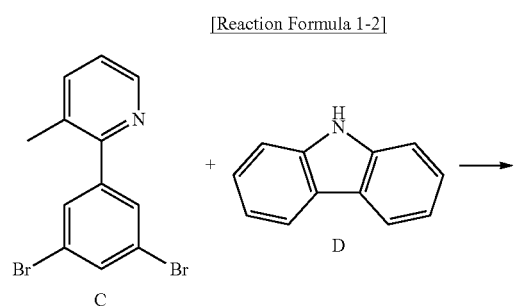

Under nitrogen condition, the compound C was dissolved in toluene, and the compound D (0.9 equivalent) was added. Sodium t-butoxide (4.0 equivalent) was added, and Pd$_2$(dba)$_3$ (0.04 equivalent) and tri-tert-butyl phosphine (0.04 equivalent) were added. The mixture was refluxed and stirred under the temperature of 80° C. for 24 hrs, and then the reaction was finished. The resultant was extracted using an organic solvent, and the organic solvent was removed. The resultant was columned and reprecipitated such that the compound E was obtained.

(3) Compound 1-2

[Reaction Formula 1-3]

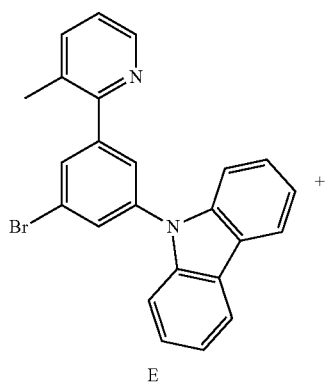

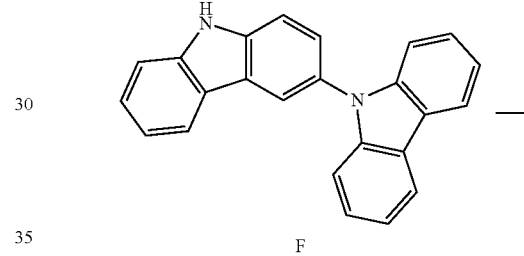

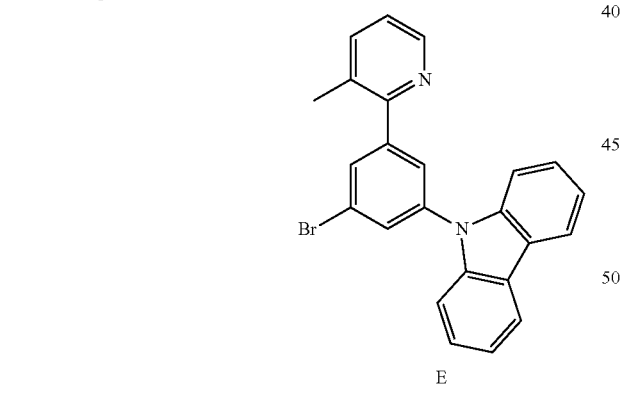

1-2

Under nitrogen condition, the compound E was dissolved in toluene, and the compound F (1.2 equivalent) was added. Sodium t-butoxide (4.4 equivalent) was added, and Pd$_2$(dba)$_3$ (0.05 equivalent) and tri-tert-butyl phosphine (0.05 equivalent) were added. The mixture was refluxed and stirred under the temperature of 80° C. for 24 hrs, and then the reaction was finished. The resultant was extracted using an organic solvent, and the organic solvent was removed. The resultant was columned and reprecipitated such that the compound 1-2 was obtained.

2. Synthesis of Compound 1-6
(1) Compound E'

[Reaction Formula 2-1]

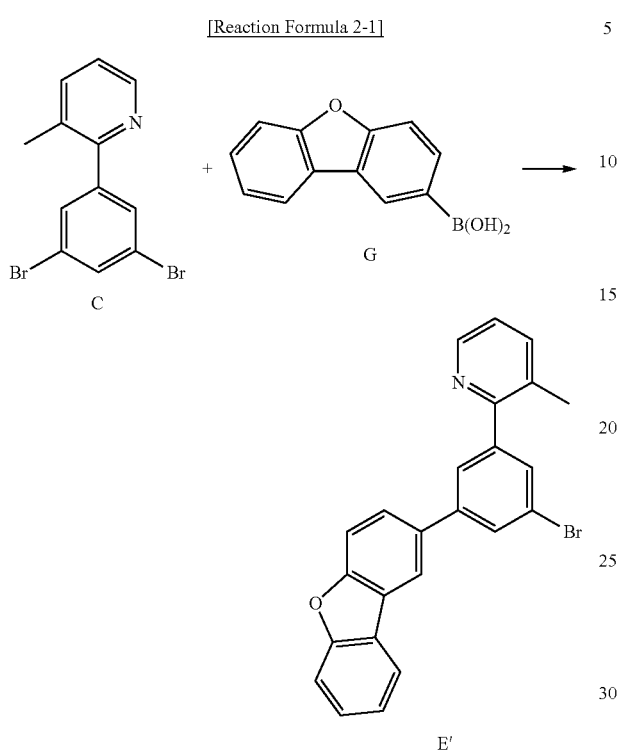

Under nitrogen condition, the compound C was dissolved in a mixed solution of tetrahydrofuran and toluene (volume ratio=5:1), and the compound G (0.9 equivalent) was added. Potassium carbonate (4.0 equivalent) was dissolved in the DI water, and Pd(0) (0.04 equivalent) were added. The reaction mixture was refluxed and stirred under the temperature of 80° C. for 8 hrs, and then the reaction was finished. The resultant was extracted using an organic solvent, and the organic solvent was removed. The resultant was columned and reprecipitated such that the compound E' was obtained.

(2) Compound 1-6

[Reaction Formula 2-2]

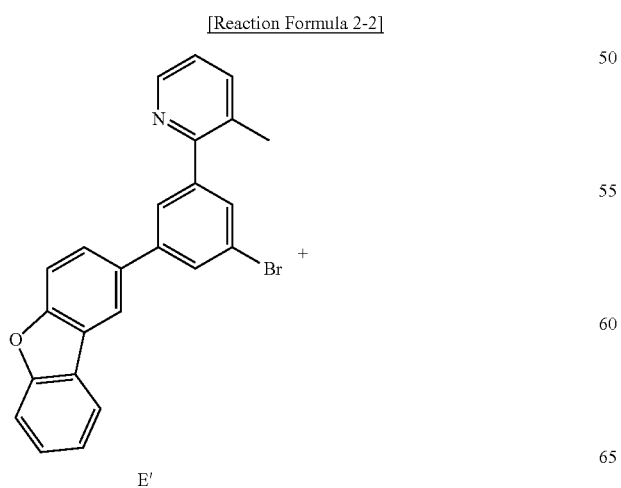

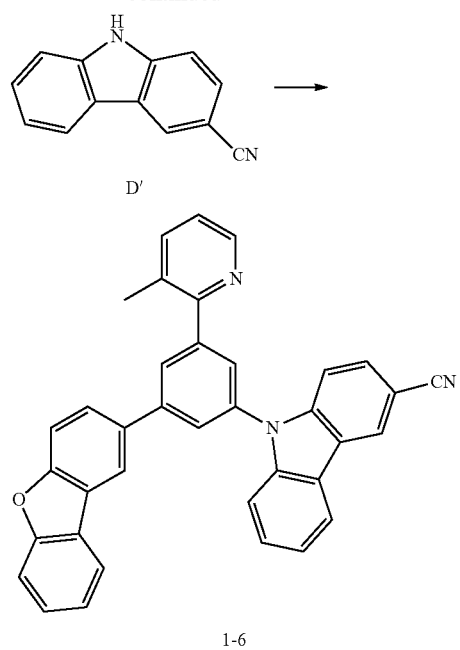

Under nitrogen condition, the compound E' was dissolved in toluene, and the compound D' (1.2 equivalent) was added. Sodium t-butoxide (4.4 equivalent) was added, and Pd$_2$(dba)$_3$ (0.05 equivalent) and tri-tert-butyl phosphine (0.05 equivalent) were added. The mixture was refluxed and stirred under the temperature of 80° C. for 24 hrs, and then the reaction was finished. The resultant was extracted using an organic solvent, and the organic solvent was removed. The resultant was columned and reprecipitated such that the compound 1-6 was obtained.

3. Synthesis of Compound 1-7
(1) Compound E"

[Reaction Formula 3-1]

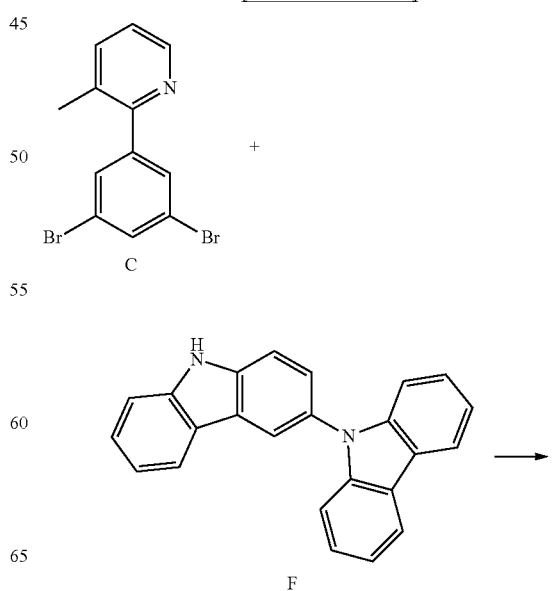

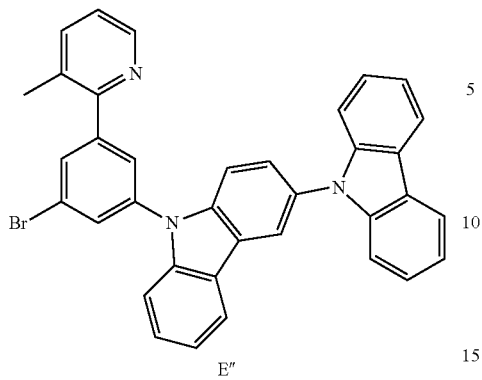

E″

Under nitrogen condition, the compound C was dissolved in toluene, and the compound F (0.9 equivalent) was added. Sodium t-butoxide (4.0 equivalent) was added, and Pd$_2$(dba)$_3$ (0.04 equivalent) and tri-tert-butyl phosphine (0.04 equivalent) were added. The mixture was refluxed and stirred under the temperature of 80° C. for 8 hrs, and then the reaction was finished. The resultant was extracted using an organic solvent, and the organic solvent was removed. The resultant was columned and reprecipitated such that the compound E″ was obtained.

(2) Compound 1-7

[Reaction Formula 3-2]

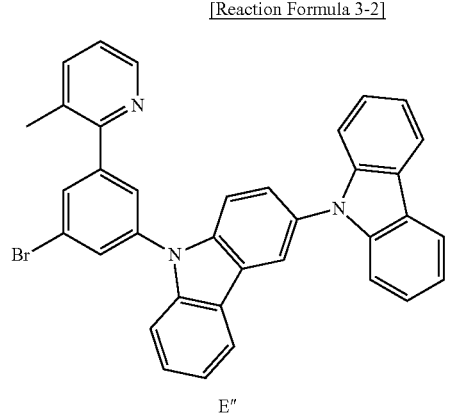

E″

+

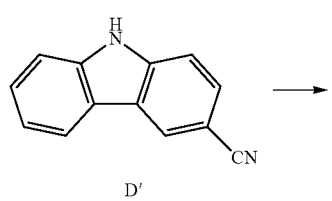

D′

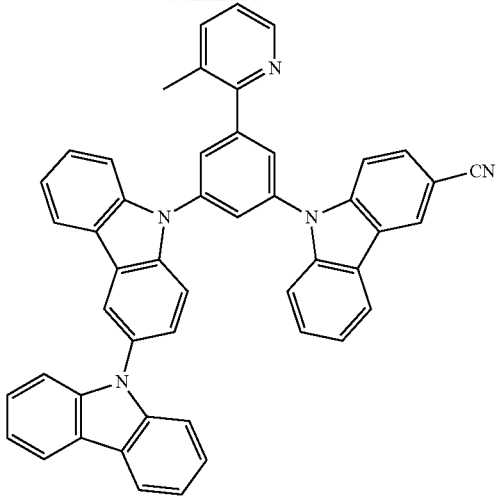

1-7

Under nitrogen condition, the compound E″ was dissolved in toluene, and the compound D′ (1.2 equivalent) was added. Sodium t-butoxide (4.4 equivalent) was added, and Pd$_2$(dba)$_3$ (0.05 equivalent) and tri-tert-butyl phosphine (0.05 equivalent) were added. The mixture was refluxed and stirred under the temperature of 80° C. for 24 hrs, and then the reaction was finished. The resultant was extracted using an organic solvent, and the organic solvent was removed. The resultant was columned and reprecipitated such that the compound 1-7 was obtained.

4. Synthesis of Compound 2-10

(1) Compound C′

[Reaction Formula 4-1]

Under nitrogen condition, the compound A′ was dissolved in a mixed solution of tetrahydrofuran and toluene (volume ratio=5:1), and the compound B′ (0.8 equivalent) was added. Potassium carbonate (4.0 equivalent) was dissolved in the DI water, and Pd(0) (0.04 equivalent) were added. The reaction mixture was refluxed and stirred under the temperature of 80° C. for 8 hrs, and then the reaction was finished. The resultant was extracted using an organic solvent, and the organic solvent was removed. The resultant was columned and reprecipitated such that the compound C′ was obtained.

(2) Compound E'''

[Reaction Formula 4-2]

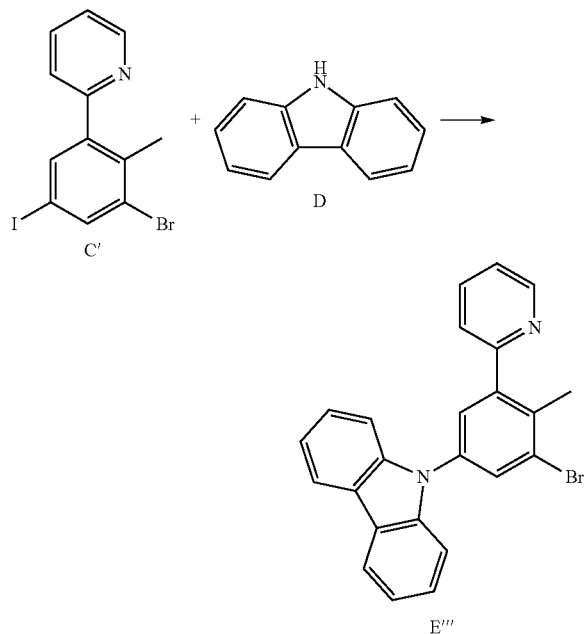

Under nitrogen condition, the compound C' was dissolved in toluene, and the compound D (0.8 equivalent) was added. Potassium phosphate (1.5 equivalent), ±-trans-1,2-diaminocyclohexane (0.2 equivalent) and CuI (0.1 equivalent) were added. The mixture was refluxed and stirred under the temperature of 80° C. for 8 hrs, and then the reaction was finished. The resultant was extracted using an organic solvent, and the organic solvent was removed. The resultant was columned and reprecipitated such that the compound E''' was obtained.

(2) Compound 2-10

[Reaction Formula 4-3]

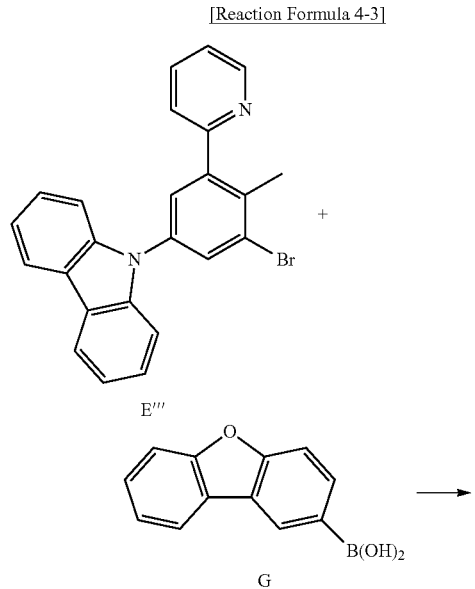

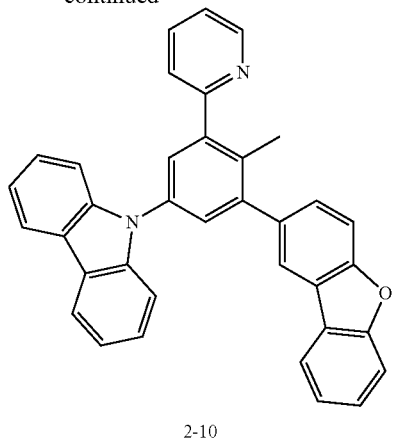

2-10

Under nitrogen condition, the compound E/// was dissolved in a mixed solution of tetrahydrofuran and toluene (volume ratio=5:1), and the compound G (1.2 equivalent) was added. Potassium carbonate (4.4 equivalent) was dissolved in the DI water, and Pd(0) (0.05 equivalent) were added. The reaction mixture was refluxed and stirred under the temperature of 80° C. for 24 hrs, and then the reaction was finished. The resultant was extracted using an organic solvent, and the organic solvent was removed. The resultant was columned and reprecipitated such that the compound 2-10 was obtained.

The properties, i.e., a HOMO level, a LUMO level and a triplet energy level (ET), of the compounds 1-1, 1-2, 1-6, 1-7, 2-1, 2-5, 2-8, 2-10, 3-1, 3-3, 3-10, 3-13, 4-1, 4-2, 4-3 and 4-4 in Formula 3 and the compound in Formula 4 are measured and listed in Table 1. (unit: [eV])

[Formula 4]

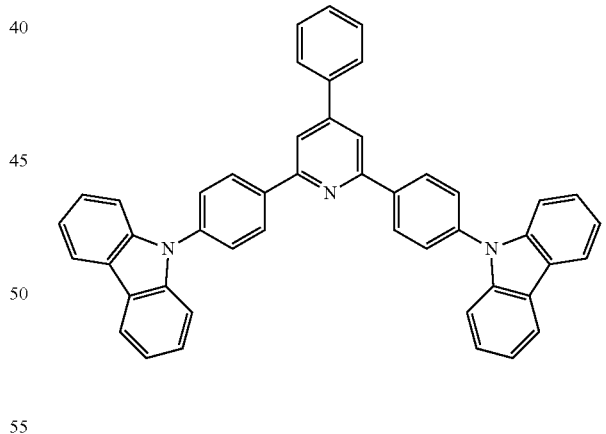

TABLE 1

|  | HOMO | LUMO | $E\gamma$ |
|---|---|---|---|
| Compound 1-1 | −5.41 | −1.18 | 3.16 |
| Compound 1-2 | −5.32 | −1.15 | 3.09 |
| Compound 1-6 | −5.79 | −1.50 | 3.18 |
| Compound 1-7 | −5.67 | −1.23 | 3.20 |
| Compound 2-1 | −5.35 | −1.12 | 3.17 |
| Compound 2-5 | −5.20 | −1.08 | 3.09 |
| Compound 2-8 | −5.26 | −1.28 | 3.01 |
| Compound 2-10 | −5.13 | −1.21 | 3.12 |
| Compound 3-1 | −5.37 | −0.99 | 3.11 |
| Compound 3-3 | −5.28 | −1.05 | 3.17 |

TABLE 1-continued

|  | HOMO | LUMO | Eγ |
|---|---|---|---|
| Compound 3-10 | −5.76 | −1.21 | 3.20 |
| Compound 3-13 | −5.73 | −1.20 | 3.18 |
| Compound 4-1 | −5.16 | −0.97 | 3.09 |
| Compound 4-2 | −5.16 | −1.19 | 3.08 |
| Compound 4-3 | −5.25 | −1.03 | 3.18 |
| Compound 4-4 | −5.59 | −1.23 | 3.20 |
| Formula 4 | −5.61 | −126 | 2.70 |

As shown in Table 1, in comparison to the compound in Formula 4, where no alkyl group is substituted to the pyridyl moiety and the phenylene linker, the organic compound of the present disclosure has higher triplet energy. Accordingly, the organic compound used as the host in the EML provides high energy efficiency. In addition, since the organic compound of the present disclosure has the n-type property, the emitting zone is shifted such that the emitting efficiency and the lifespan of the organic light emitting diode and the OLED device are improved.

[Organic Light Emitting Diode]

In the vacuum chamber of about $10^{-7}$ Torr, layers are sequentially deposited on an ITO substrate.

(a) HIL (50 Å, HATCN), (b) HTL (500 Å, NPB), (c) EBL (100 Å, mCP), (d) EML (300 Å, HOST: Dopant (30 wt %, Formula 5)), (e) ETL (300 Å, TPBI), (f) EIL (10 Å, LiF), and (g) Cathode (1000 Å, Al)

[Formula 5]

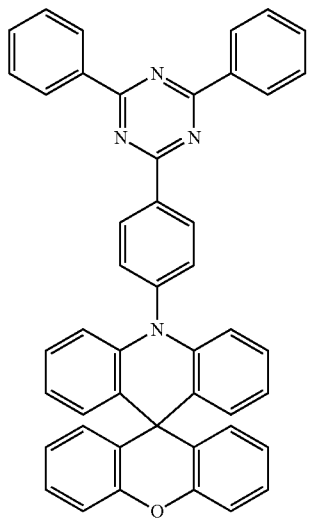

(1) Comparative Example 1 (Ref1)

The compound of Formula 6 is used as the host.

(2) Comparative Example 2 (Ref2)

The compound of Formula 7 is used as the host.

(3) Example 1 (Ex1)

The compound 1-2 of Formula 3 is used as the host.

(4) Example 2 (Ex2)

The compound 1-6 of Formula 3 is used as the host.

(5) Example 3 (Ex3)

The compound 1-7 of Formula 3 is used as the host.

(6) Example 4 (Ex4)

The compound 2-10 of Formula 3 is used as the host.

[Formula 6]

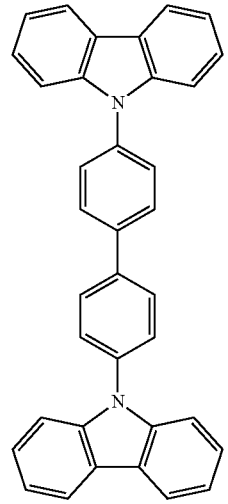

[Formula 7]

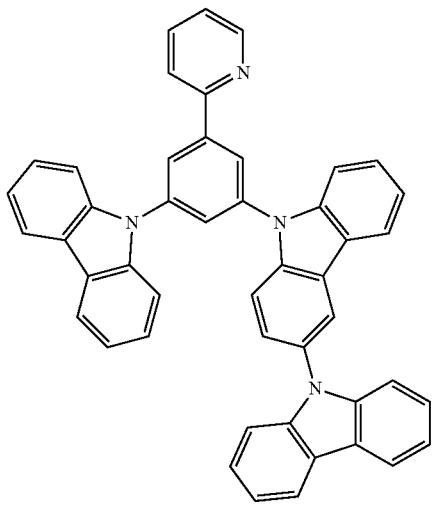

The properties of the organic light emitting diodes of Ref1, Ref2 and Ex1 to Ex4 are measured. The driving voltage, the external quantum efficiency (EQE), the power efficiency (lm/W), the CIE color coordinate of the organic light emitting diodes are listed in Table 2.

TABLE 2

|  | V | EQE [%] | CIEy |
|---|---|---|---|
| Ref 1 | 4.5 | 6.4 | 0.343 |
| Ref 2 | 4.1 | 8.8 | 0.337 |
| EX 1 | 3.7 | 13.2 | 0.334 |
| Ex 2 | 3.2 | 12.2 | 0.335 |
| Ex 3 | 3.7 | 14.5 | 0.339 |
| Ex 4 | 3.4 | 14.1 | 0.338 |

As shown in Table 2, in comparison to the organic light emitting diodes of Ref1 and Ref2, the emitting efficiency, e.g., the EQE and the power efficiency, of the organic light emitting diodes of Ex1 to Ex4 using the organic compounds of the present disclosure as the host is remarkably increased.

Figure 7:
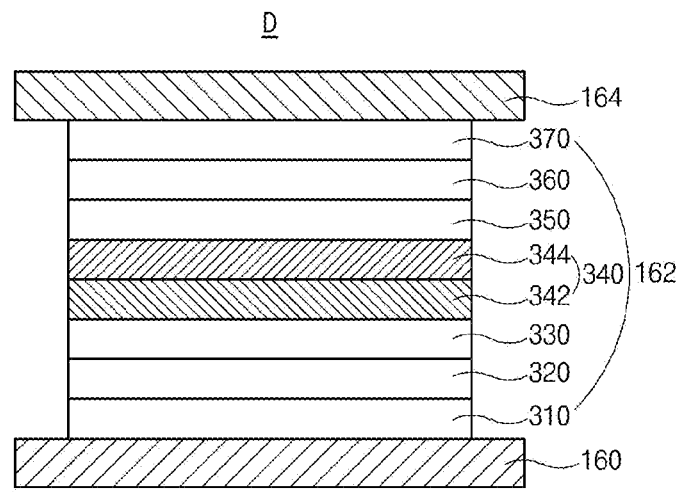
FIG. 7 is a schematic cross-sectional view of an organic light emitting diode of the present disclosure.

FIG. 7 is a schematic cross-sectional view of an organic light emitting diode of the present disclosure.

As shown in FIG. 7, an organic light emitting diode D includes the first and second electrodes 160 and 164, which face each other, and the organic emitting layer 162 therebetween. The organic emitting layer 162 includes an EML 340, which includes first and second layers 342 and 344 and is positioned between the first and second electrodes 160 and 164, a HTL 320 between the first electrode 160 and the EML 340 and an ETL 360 between the second electrode 164 and the EML 340.

In addition, the organic emitting layer 162 may further include a HIL 310 between the first electrode 160 and the HTL 320 and an EIL 370 between the second electrode 164 and the ETL 360.

Moreover, the organic emitting layer 162 may further include an EBL 330 between the HTL 320 and the EML 340 and a HBL 350 between the EML 340 and the ETL 360.

For example, in the EML 340, the first layer 342 (e.g., a first emitting material layer) may include the organic compound of the present disclosure as a first host and a delayed fluorescent dopant as a first dopant, and the second layer 344 (e.g., a second emitting material layer) may include a second host and a fluorescent dopant as a second dopant. Alternatively, the second layer 344 may include the organic compound of the present disclosure as a first host and a delayed fluorescent dopant as a first dopant, and the first layer 342 may include a second host and a fluorescent dopant as a second host. The second host may be the organic compound of the present disclosure. The delayed fluorescent dopant has a singlet energy being larger than the fluorescent dopant.

The organic light emitting diode, where the first layer 342 includes the delayed fluorescent dopant and the second layer 344 includes the fluorescent dopant, will be explained.

In the organic light emitting diode D, the singlet energy and the triplet energy of the delayed fluorescent dopant are transferred into the fluorescent dopant such that the emission is generated from the fluorescent dopant. Accordingly, the quantum efficiency of the organic light emitting diode D is increased, and the FWHM of the organic light emitting diode D is narrowed.

The delayed fluorescent dopant as the first dopant has high quantum efficiency. However, since the light emitted from the delayed fluorescent dopant has wide FWHM, the light from the delayed fluorescent dopant has bad color purity. On the other hand, the fluorescent dopant as the second dopant has narrow FWHM and high color purity. However, since the triplet energy of the fluorescent dopant is not engaged in the emission, the fluorescent dopant has low quantum efficiency.

Since the EML 340 of the organic light emitting diode D in the present disclosure includes the first layer 342, which includes the delayed fluorescent dopant, and the second layer 344, which includes the fluorescent dopant, the organic light emitting diode D has advantages in both the emitting efficiency and the color purity.

The triplet energy of the delayed fluorescent dopant is converted into the singlet energy of the delayed fluorescent dopant by the RISC effect, and the singlet energy of the delayed fluorescent dopant is transferred into the singlet energy of the fluorescent dopant. Namely, the difference between the triplet energy of the delayed fluorescent dopant and the singlet energy of the delayed fluorescent dopant is less than 0.3 eV such that the triplet energy of the delayed fluorescent dopant is converted into the singlet energy of the delayed fluorescent dopant by the RISC effect.

As a result, the delayed fluorescent dopant has an energy transfer function, and the first layer 342 including the delayed fluorescent dopant is not engaged in the emission. The emission is generated in the second layer 344 including the fluorescent dopant.

The triplet energy of the delayed fluorescent dopant is converted into the singlet energy of the delayed fluorescent dopant by the RISC effect. In addition, since the singlet energy of the delayed fluorescent dopant is higher than that of the fluorescent dopant, the singlet energy of the delayed fluorescent dopant is transferred into the singlet energy of the fluorescent dopant. As a result, the fluorescent dopant emits the light using the singlet energy and the triplet energy such that the quantum efficiency (emitting efficiency) of the organic light emitting diode D is improved.

In other words, the organic light emitting diode D and the OLED device 100 (of FIG. 2) including the organic light emitting diode D has advantages in both the emitting efficiency and the color purity.

In each of the first and second layers 342 and 344, the first and second hosts may have a percentage by weight being larger than the delayed fluorescent dopant and the fluorescent dopant, respectively. In addition, the percentage by weight of the delayed fluorescent dopant in the first layer 342 may be greater than that of the fluorescent dopant in the second layer 344. As a result, the energy transfer from the delayed fluorescent dopant into the fluorescent dopant is sufficiently generated.

The singlet energy of the first host is greater than that of the delayed fluorescent dopant, and the triplet energy of the first host is greater than that of the delayed fluorescent dopant. In addition, the singlet energy of the second host is greater than that of the fluorescent dopant.

When not satisfying this condition, a quenching happens at the first and second dopants or an energy transfer from the host to the dopant does not happen, and thus the quantum efficiency of the organic light emitting diode D may be reduced.

As mentioned above, since the organic compound of the present disclosure has high triplet energy, the energy transfer efficiency into the delayed fluorescent compound is increased such that the emitting efficiency of the organic light emitting diode D is improved.

In addition, since the organic compound of the present disclosure having the n-type property is included in the EML as the host, the quenching problem of the exciton by an interaction between the triplet exciton of the dopant and the hole-polaron is prevented such that the emitting efficiency of the organic light emitting diode D is further improved.

For example, the second host, which is included in the second layer 344 with the fluorescent dopant, may be same as a material of the HBL 350. In this instance, the second layer 344 may have a hole blocking function with an emission function. Namely, the second layer 344 may serve as a buffer layer for blocking the hole. When the HBL 350 is omitted, the second layer 344 serves as an emitting layer and a hole blocking layer.

When the first layer 342 includes the fluorescent dopant and the second layer 344 includes the delayed fluorescent dopant, the first host of the first layer 342 may be same as a material of the EBL 330. In this instance, the first layer 342 may have an electron blocking function with an emission function. Namely, the first layer 342 may serve as a buffer layer for blocking the electron. When the EBL 330 is omitted, the first layer 342 serves as an emitting layer and an electron blocking layer.

Figure 8:
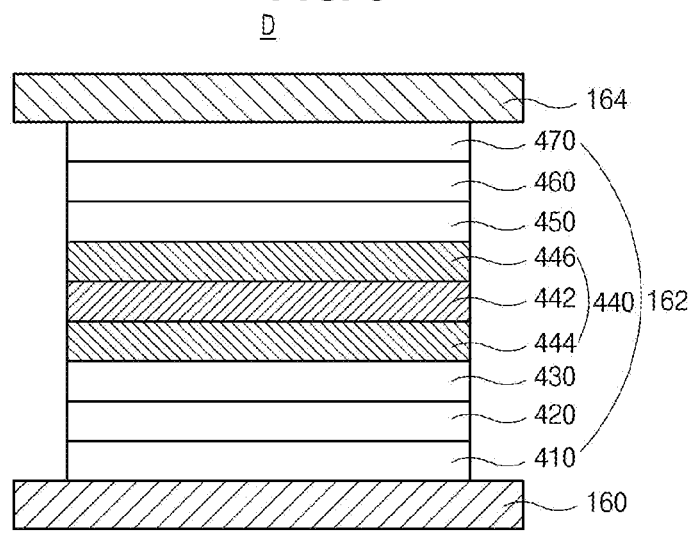
FIG. 8 is a schematic cross-sectional view of an organic light emitting diode of the present disclosure.

FIG. 8 is a schematic cross-sectional view of an organic light emitting diode of the present disclosure.

As shown in FIG. 8, an organic light emitting diode D includes the first and second electrodes 160 and 164, which face each other, and the organic emitting layer 162 therebetween. The organic emitting layer 162 includes an EML 440, which includes first to third layers 442, 444 and 446 and is positioned between the first and second electrodes 160 and 164, a HTL 420 between the first electrode 160 and the EML 440 and an ETL 460 between the second electrode 164 and the EML 440.

In addition, the organic emitting layer 162 may further include a HIL 410 between the first electrode 160 and the HTL 420 and an EIL 470 between the second electrode 164 and the ETL 460.

Moreover, the organic emitting layer 162 may further include an EBL 430 between the HTL 420 and the EML 440 and a HBL 450 between the EML 440 and the ETL 460.

In the EML 440, the first layer 442 is positioned between the second layer 444 and the third layer 446. Namely, the second layer 444 is positioned between the EBL 430 and the first layer 442, and the third layer 446 is positioned between the first layer 442 and the HBL 450.

The first layer 442 (e.g., a first emitting material layer) may include the organic compound of the present disclosure as a first host and a delayed fluorescent dopant as a first dopant, and the second layer 444 (e.g., a second emitting material layer) may include a second host and a fluorescent dopant as a second dopant. The third layer 446 (e.g., a third emitting material layer) may include a third host and a fluorescent dopant as a third dopant. The fluorescent dopant in the second and third layers 444 and 446 may be same or different. The second and third hosts may be the organic compound of the present disclosure. The delayed fluorescent dopant has a singlet energy being larger than the fluorescent dopant.

In the organic light emitting diode D, the singlet energy and the triplet energy of the delayed fluorescent dopant are transferred into the fluorescent dopant in the second layer 444 and/or the third layer 446 such that the emission is generated from the fluorescent dopant.

In each of the first to third layers 442, 444 and 446, the first to third hosts may have a percentage by weight being larger than the first to third dopants, respectively. In addition, the percentage by weight of the delayed fluorescent dopant (i.e., the first dopant) in the first layer 442 may be greater than that of each of the fluorescent dopant (i.e., the second dopant) in the second layer 444 and the fluorescent dopant (i.e., the third dopant) in the third layer 446.

The singlet energy of the first host is greater than that of the delayed fluorescent dopant, and the triplet energy of the first host is greater than that of the delayed fluorescent dopant. In addition, the singlet energy of the second host is greater than that of the fluorescent dopant in the second layer 444, and the singlet energy of the third host is greater than that of the fluorescent dopant in the third layer 446.

As mentioned above, since the organic compound of the present disclosure has high triplet energy, the energy transfer efficiency into the delayed fluorescent compound is increased such that the emitting efficiency of the organic light emitting diode D is improved.

In addition, since the organic compound of the present disclosure having the n-type property is included in the EML as the host, the quenching problem of the exciton by an interaction between the triplet exciton of the dopant and the hole-polaron is prevented such that the emitting efficiency of the organic light emitting diode D is further improved.

For example, the second host in the second layer 444 may be same as a material of the EBL 430. In this instance, the second layer 444 may have an electron blocking function with an emission function. Namely, the second layer 444 may serve as a buffer layer for blocking the electron. When the EBL 430 is omitted, the second layer 444 serves as an emitting layer and an electron blocking layer.

The third host in the third layer 446 may be same as a material of the HBL 450. In this instance, the third layer 446 may have a hole blocking function with an emission function. Namely, the third layer 446 may serve as a buffer layer for blocking the hole. When the HBL 450 is omitted, the third layer 446 serves as an emitting layer and a hole blocking layer.

The second host in the second layer 444 may be same as a material of the EBL 430, and the third host in the third layer 446 may be same as a material of the HBL 450. In this instance, the second layer 444 may have an electron blocking function with an emission function, and the third layer 446 may have a hole blocking function with an emission function. Namely, the second layer 444 may serve as a buffer layer for blocking the electron, and the third layer 446 may serve as a buffer layer for blocking the hole. When the EBL 430 and the HBL 450 are omitted, the second layer 444 serves as an emitting layer and an electron blocking layer and the third layer 446 serves as an emitting layer and a hole blocking layer.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. An organic light emitting diode, comprising:
a first electrode;
a second electrode facing the first electrode; and
a first emitting material layer between the first and second electrodes and including a delayed fluorescent compound as a first dopant, and an organic compound as a first host, the organic compound is of formula:

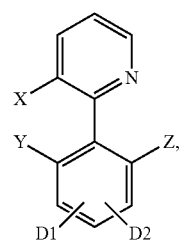

wherein each of X, Y, and Z is independently selected from hydrogen and a C1 to C20 alkyl group, and at least one of Y and Z is selected from the C1 to C20 alkyl group, and
wherein each of D1 and D2 is independently selected from a C10 to C60 heteroaryl group.

2. The organic light emitting diode according to claim 1, wherein at least one of Y and Z is methyl, and each of D1 and D2 is selected from the group consisting of substituted or non-substituted carbazolyl, substituted or non-substituted dibenzofuranyl and substituted or non-substituted dibenzothiophenyl.

3. The organic light emitting diode according to claim 2, wherein each of D1 and D2 is substituted by a carbazole group or a cyano group.

4. The organic light emitting diode according to claim 1, wherein the organic compound is selected from the group consisting of:

2-1
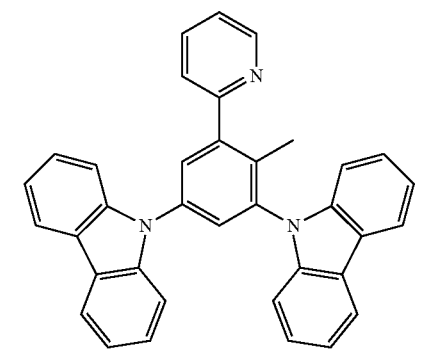

2-2
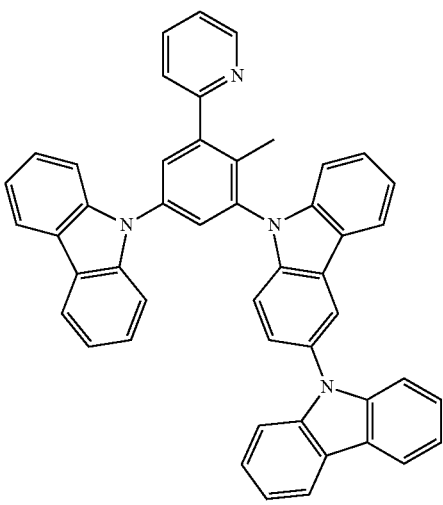

2-3
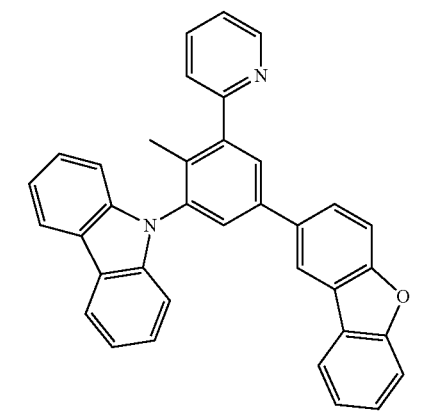

2-4
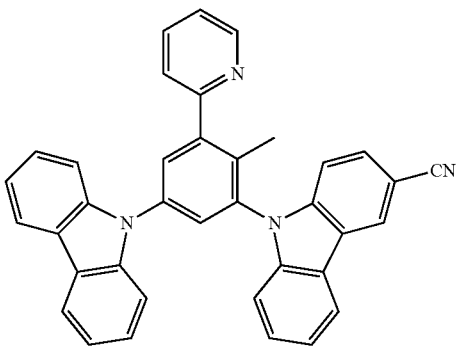

2-5
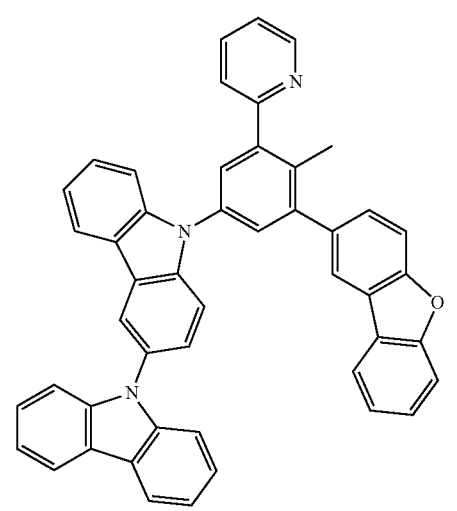

2-6
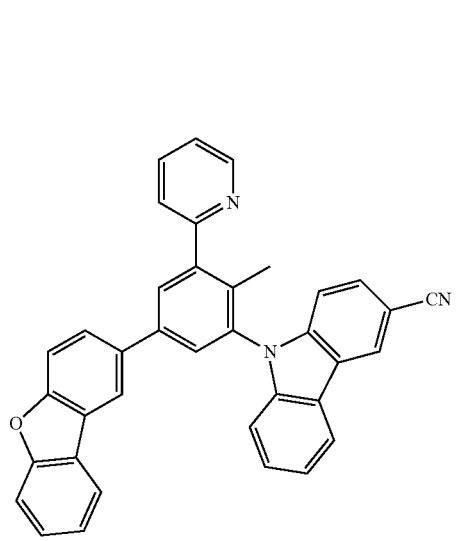

2-7
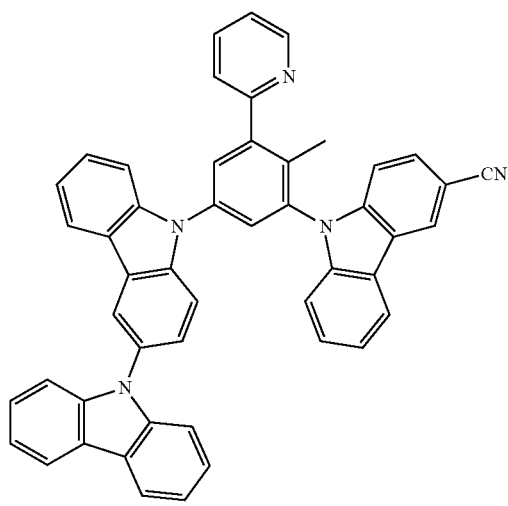
2-8
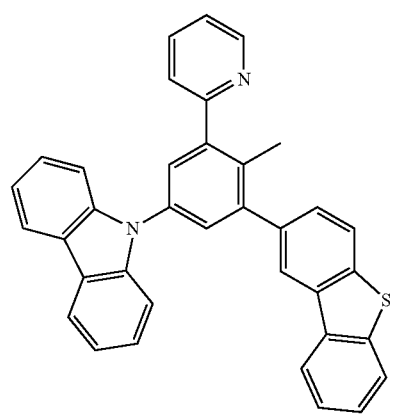
2-9
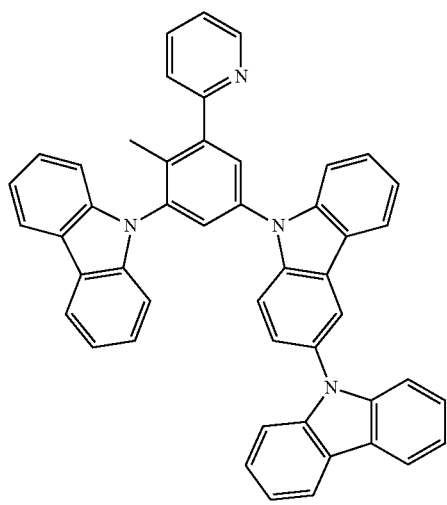
2-10
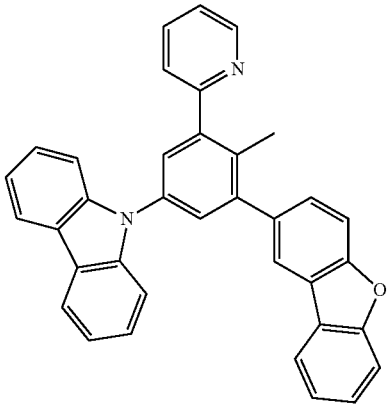
2-11
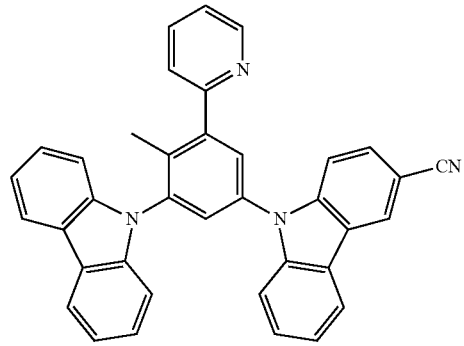
2-12
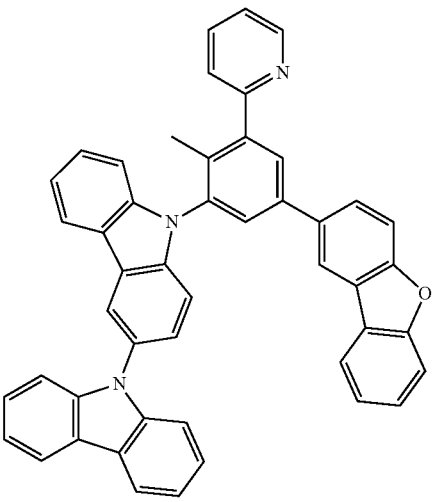

-continued
2-13
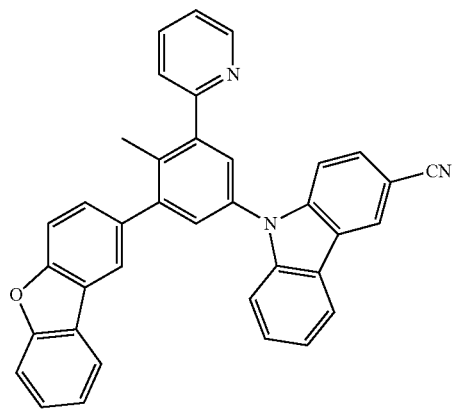
2-14
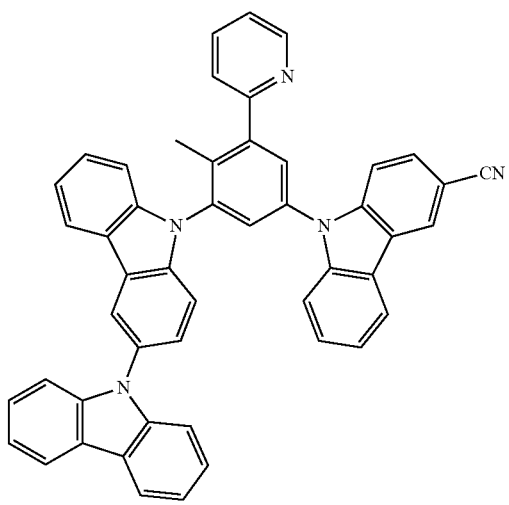
2-15
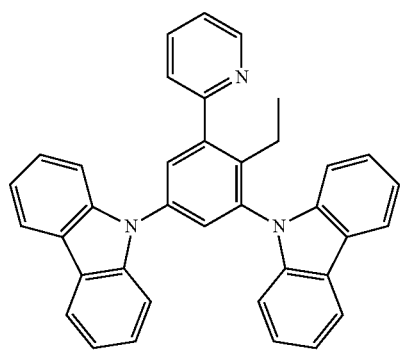
-continued
2-16
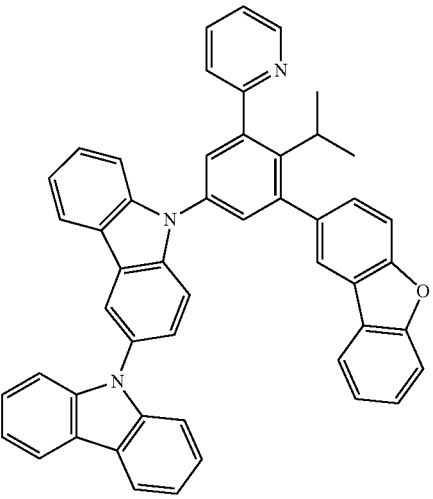
2-17
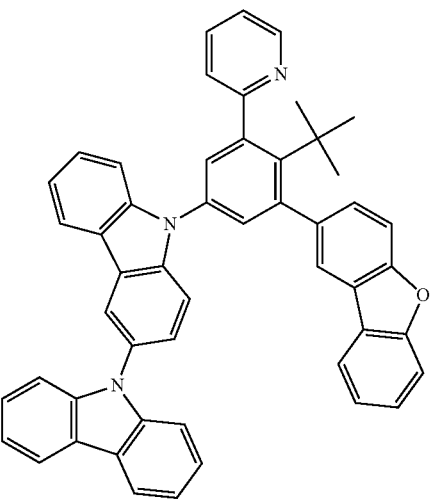
2-18
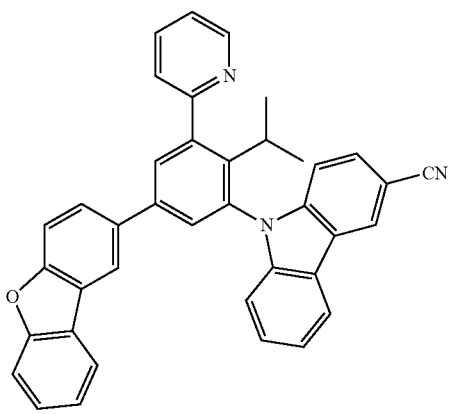

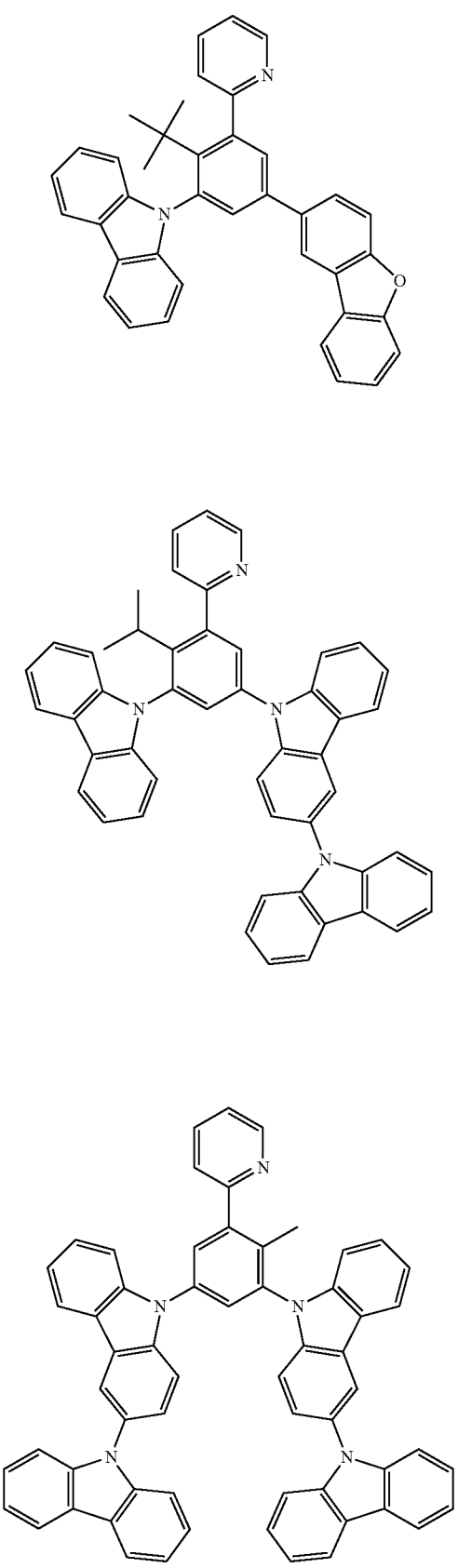
2-19
2-20
2-21
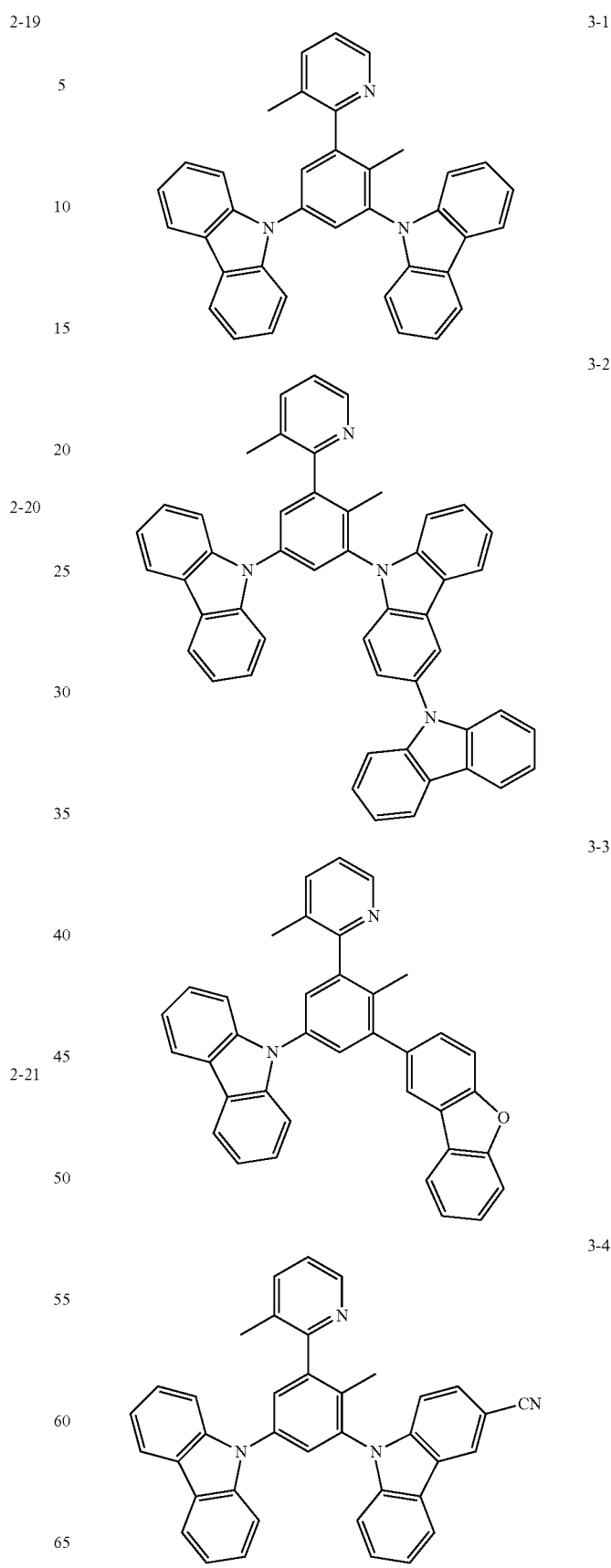
3-1
3-2
3-3
3-4

-continued
3-5
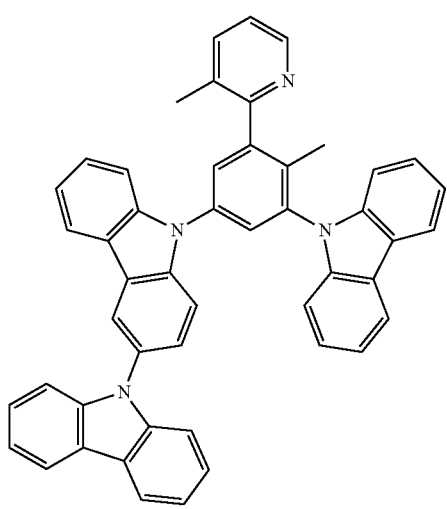
3-6
3-7
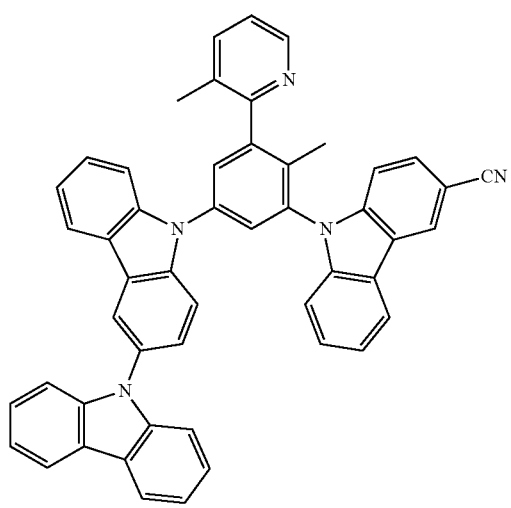
-continued
3-8
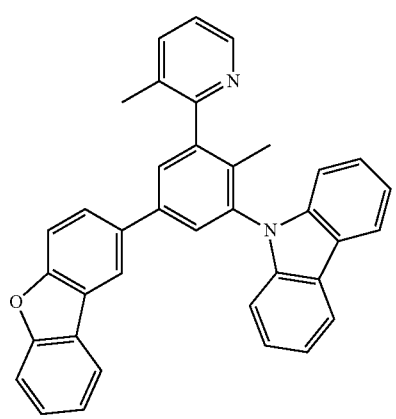
3-9
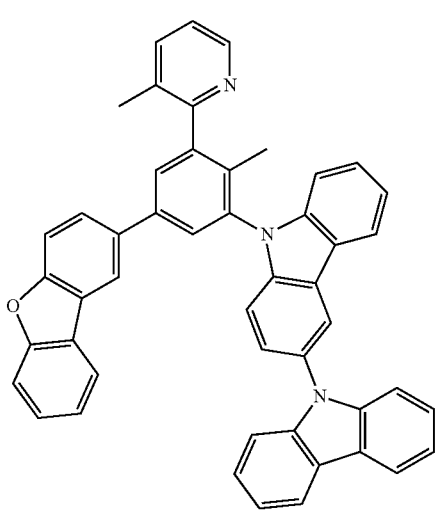
3-10

-continued
3-11
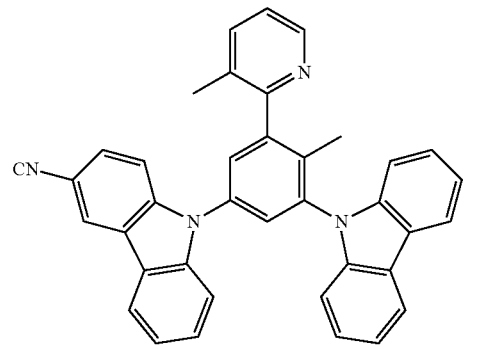
3-12
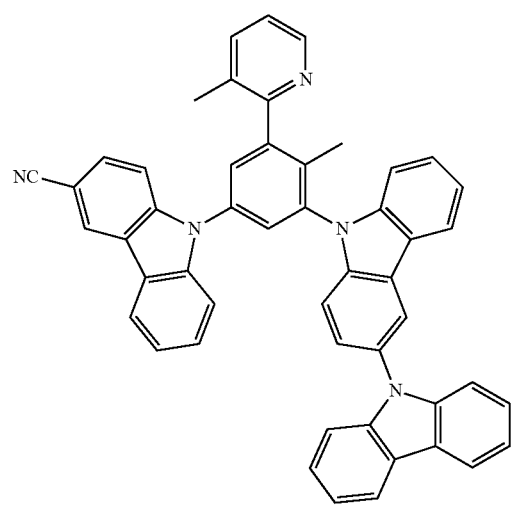
3-13
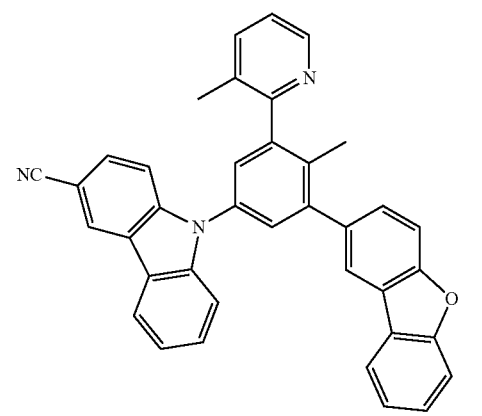
3-14
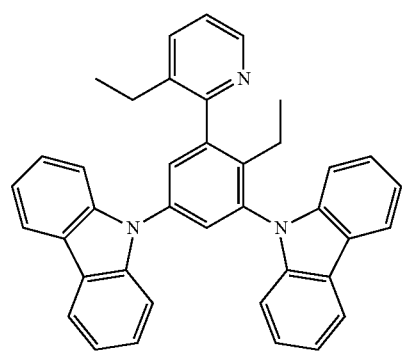
-continued
3-15
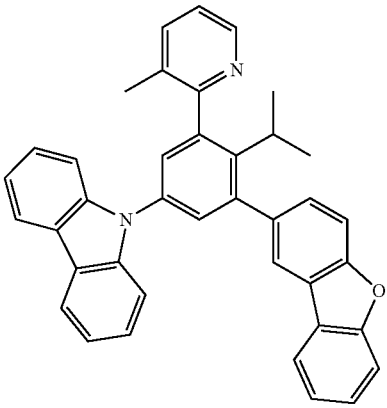
3-16
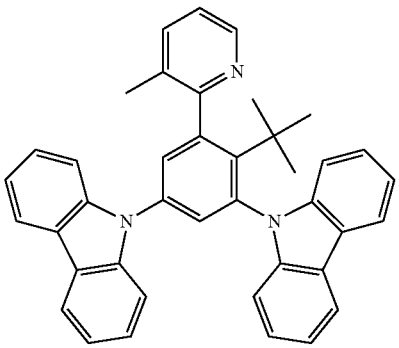
3-17
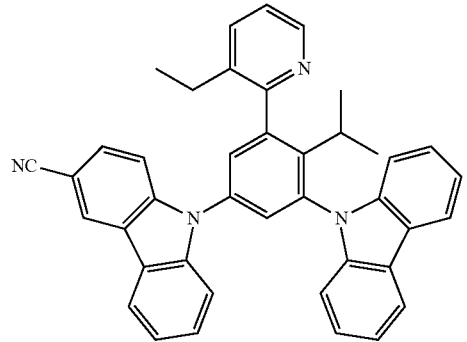
3-18
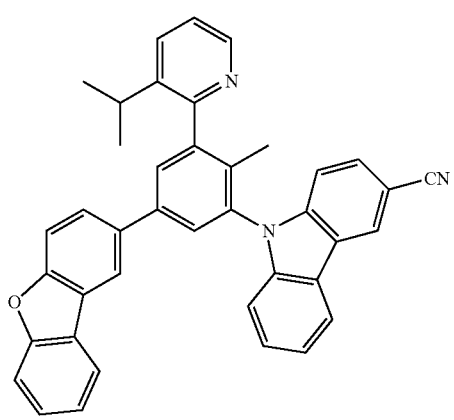

3-19
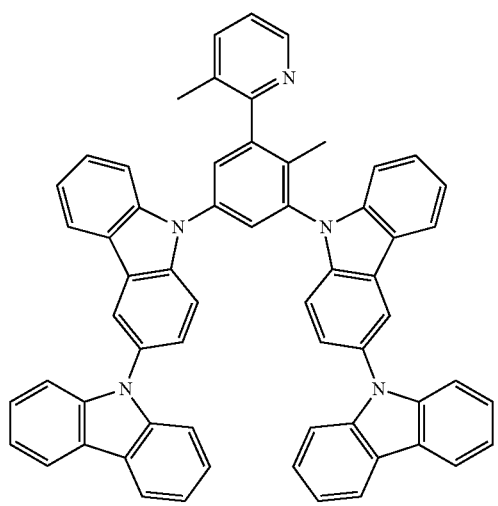
4-3
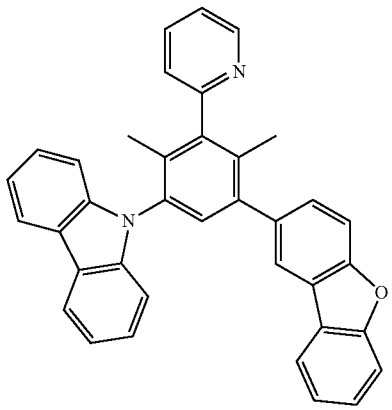
4-1
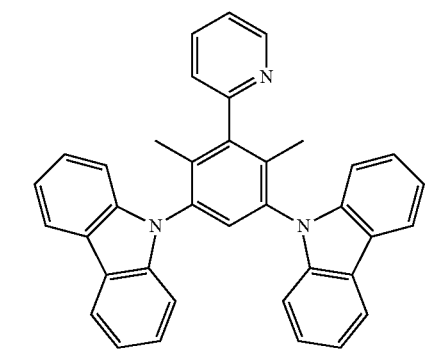
4-4
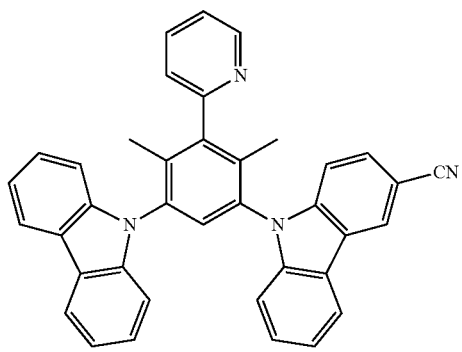
4-2
4-5
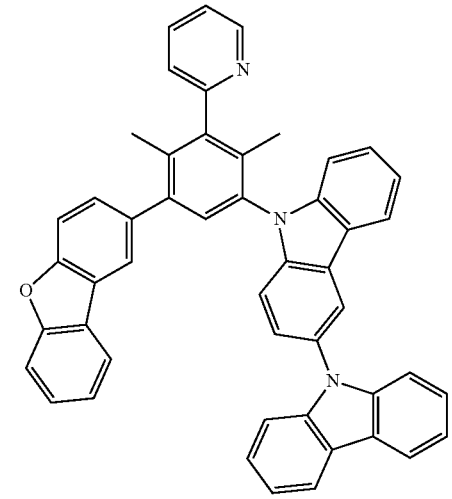

4-6
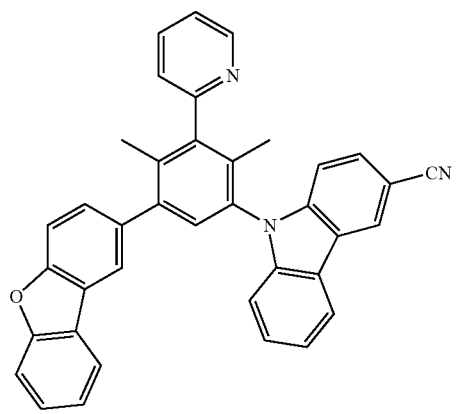
4-9
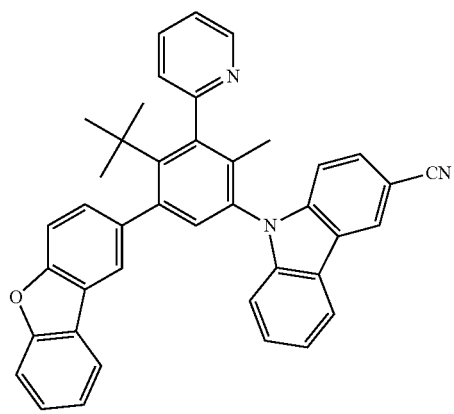
4-7
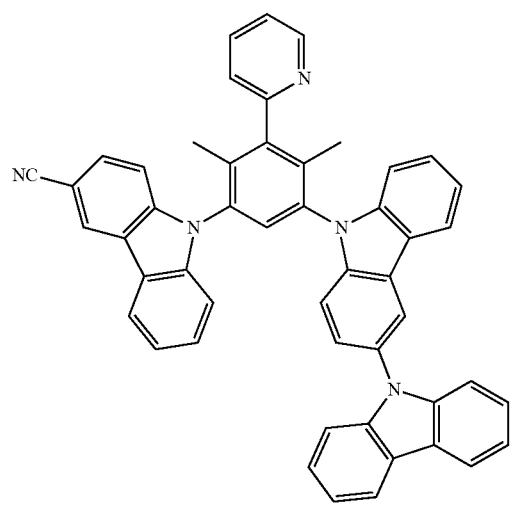
4-10
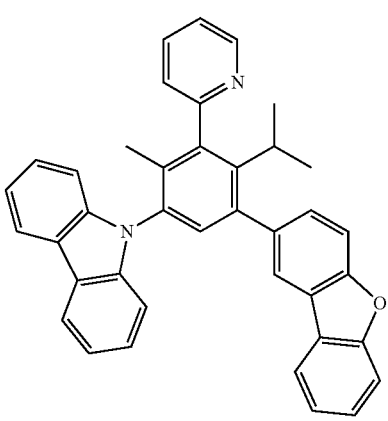
4-8
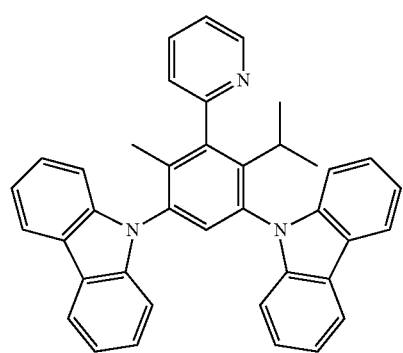
4-11
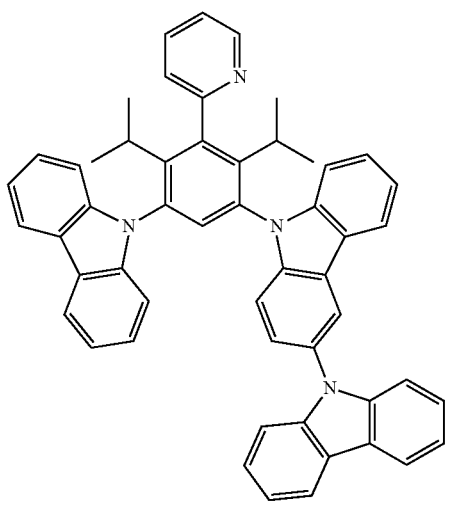

-continued 4-12

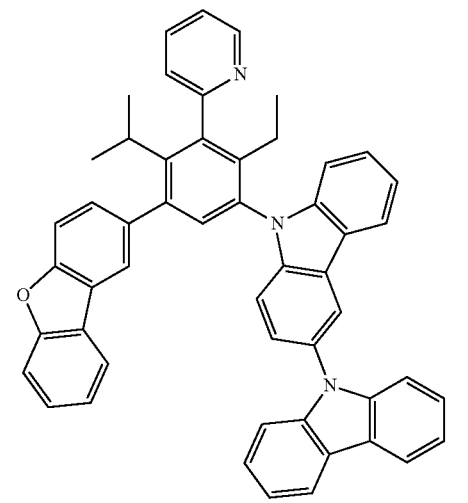

4-13

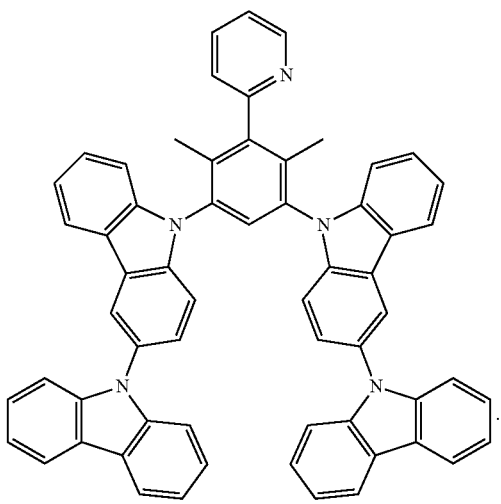

5. The organic light emitting diode according to claim 1, wherein the first dopant is:

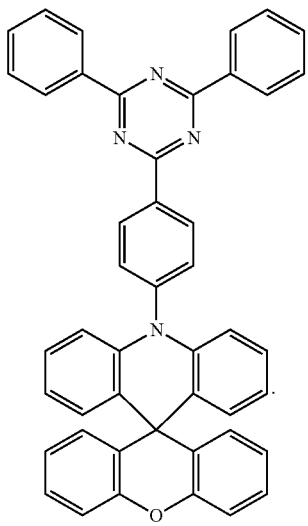 [SMILES: c1ccc(-c2nc(-c3ccccc3)nc(-c3ccc(N4c5ccccc5C5(c6ccccc6Oc6ccccc65)c5ccccc54)cc3)n2)cc1]

6. The organic light emitting diode according to claim 1, wherein the first emitting material layer further includes a fluorescent compound as a second dopant.

7. The organic light emitting diode according to claim 6, wherein the first host is:

2-10

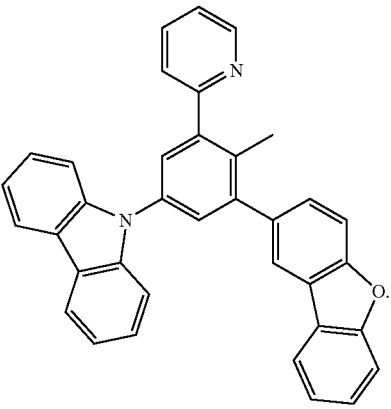

8. The organic light emitting diode according to claim 1, further comprising:
 a second emitting material layer including a second host and a fluorescent compound as a second dopant and positioned between the first electrode and the first emitting material layer.

9. The organic light emitting diode according to claim 8, further comprising:
 a third emitting material layer including a third host and a fluorescent compound as a third dopant and positioned between the second electrode and the first emitting material layer.

10. An organic light emitting display device, comprising:
 a substrate;
 an organic light emitting diode disposed on or over the substrate, the organic light emitting diode including:
  a first electrode;
  a second electrode facing the first electrode; and
  a first emitting material layer between the first and second electrodes; and
 a thin film transistor positioned between the substrate and the organic light emitting diode and connected to the organic light emitting diode,
 wherein the first emitting material layer includes a delayed fluorescent compound as a first dopant, and an organic compound as a first host, the organic compound is of formula:

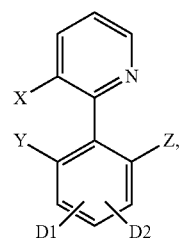

wherein each of X, Y, and Z is independently selected from hydrogen and a C1 to C20 alkyl group, and at least one of Y and Z is selected from the C1 to C20 alkyl group, and wherein each of D1 and D2 is independently selected from a C10 to C60 heteroaryl group.

11. The organic light emitting display device according to claim 10, wherein at least one of Y and Z is methyl, and each of D1 and D2 is selected from the group consisting of substituted or non-substituted carbazolyl, substituted or non-substituted dibenzofuranyl and substituted or non-substituted dibenzothiophenyl.

12. The organic light emitting display device according to claim 11, wherein each of D1 and D2 is substituted by a carbazole group or a cyano group.

13. The organic light emitting display device according to claim 10, wherein the organic compound is selected from the group consisting of:

2-1

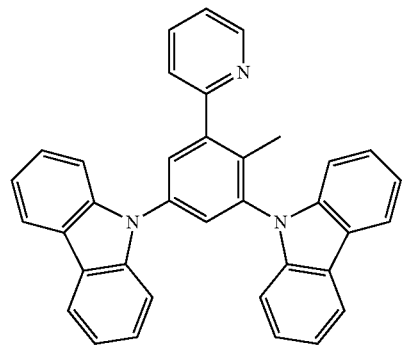

2-2

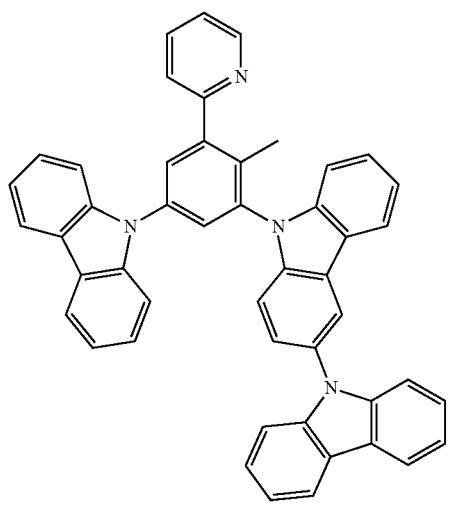

2-3

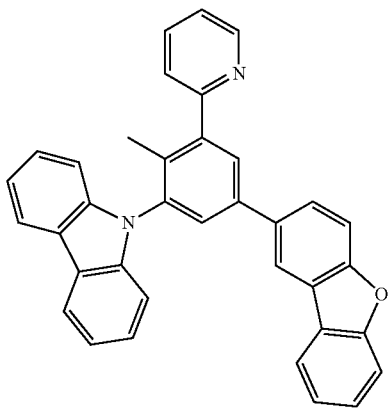

2-4

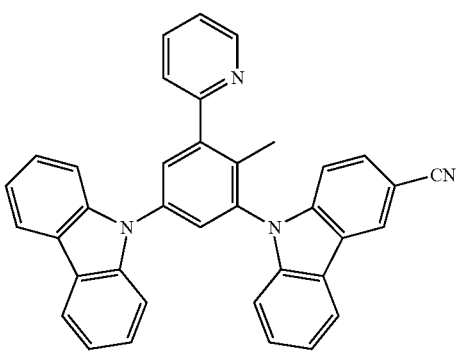

2-5

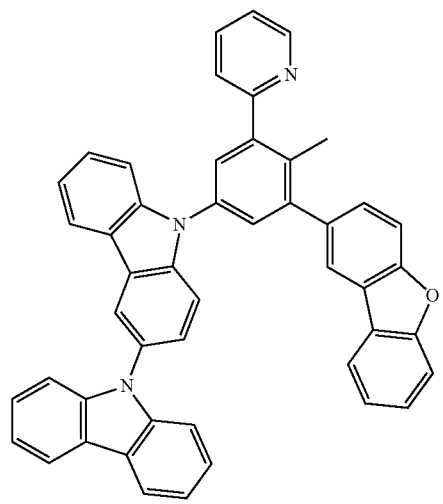

2-6
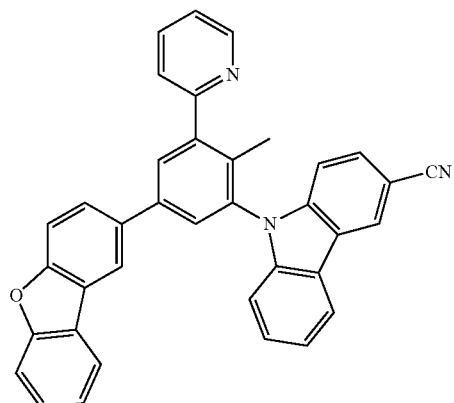
2-7
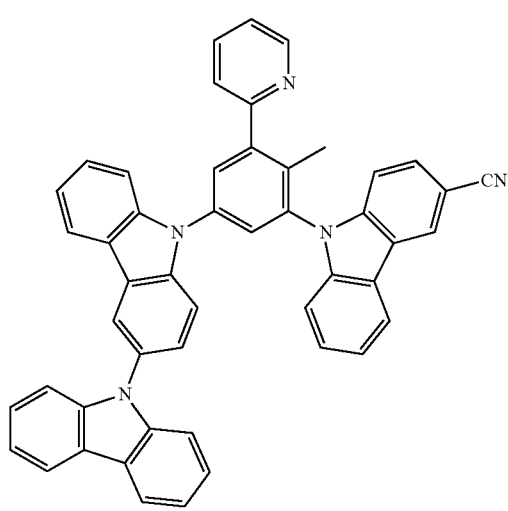
2-8
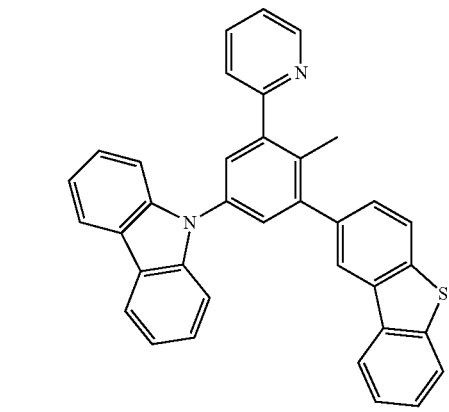
2-9
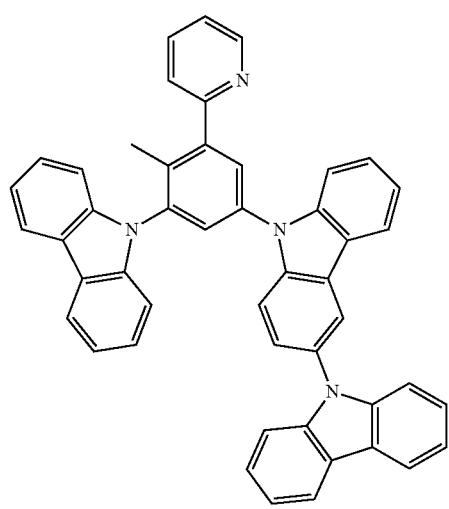
2-10
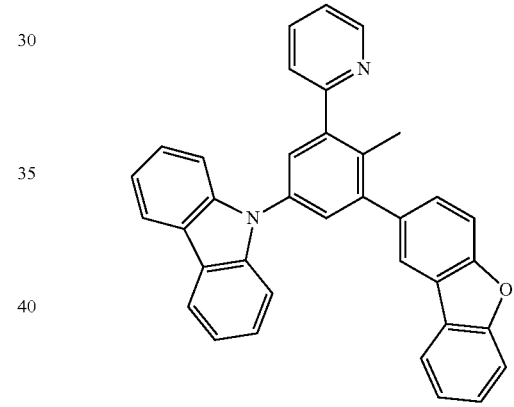
2-11
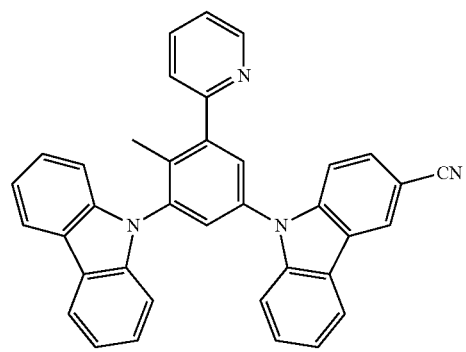

2-12
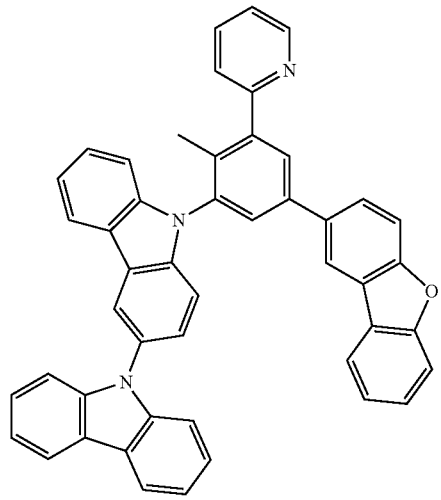
2-13
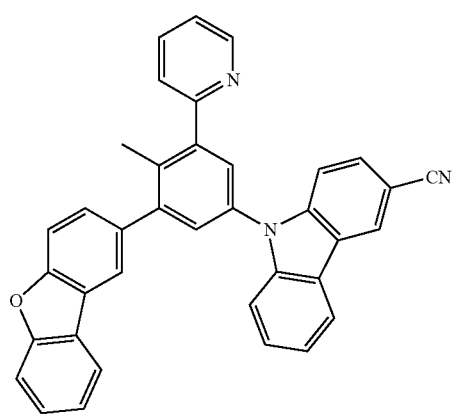
2-14
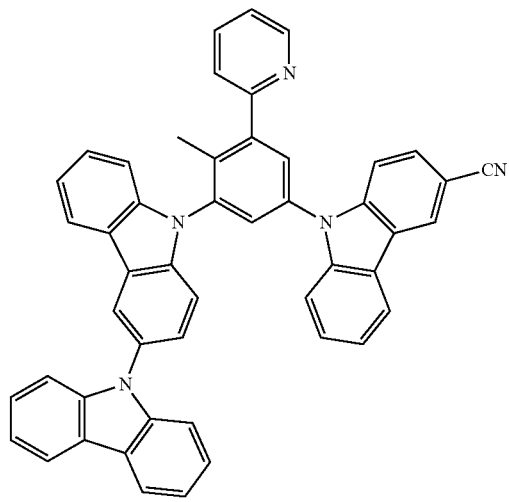
2-15
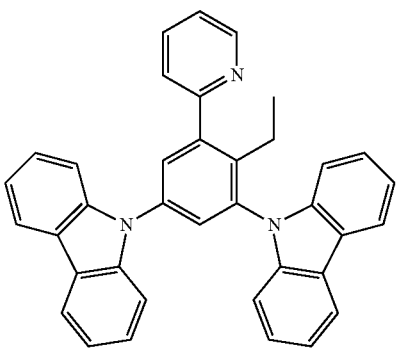
2-16
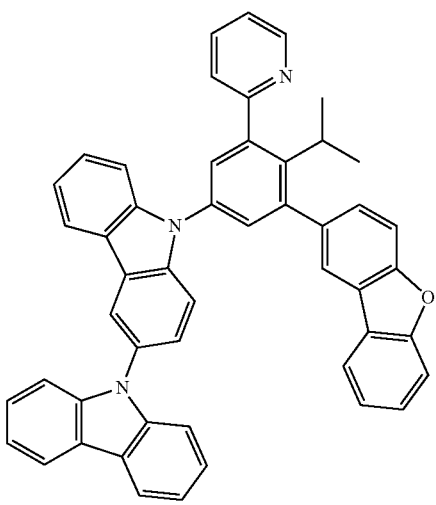
2-17
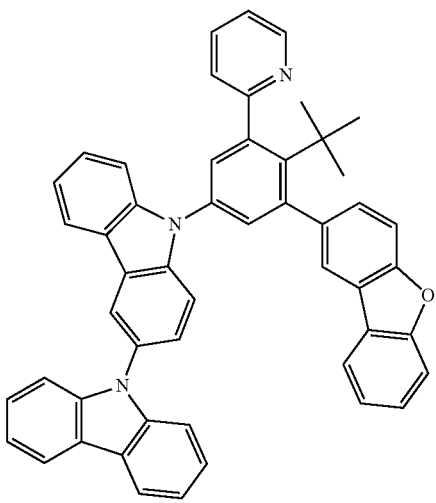

2-18
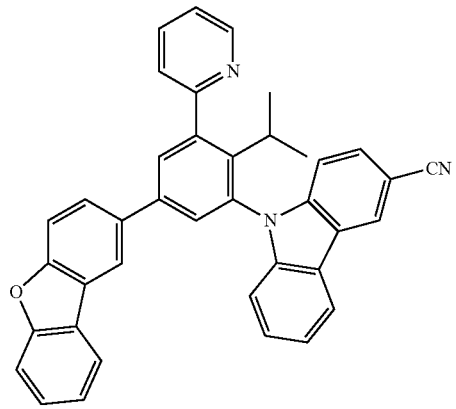
2-21
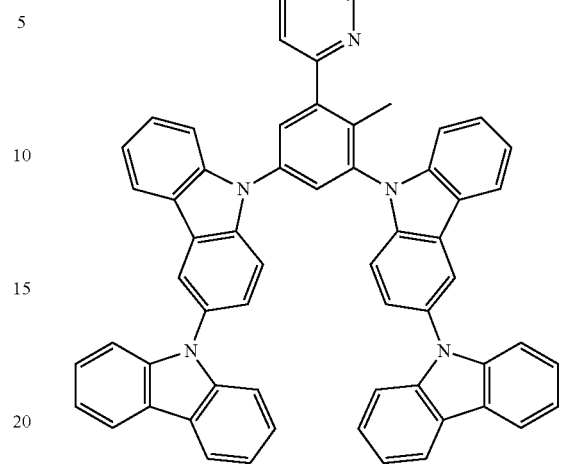
2-19
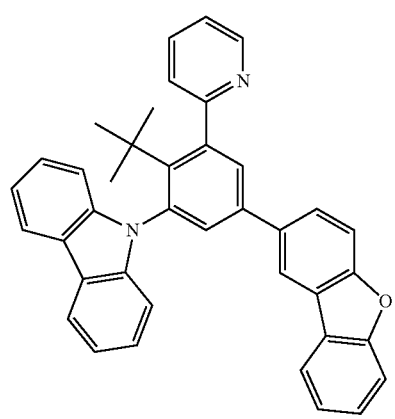
3-1
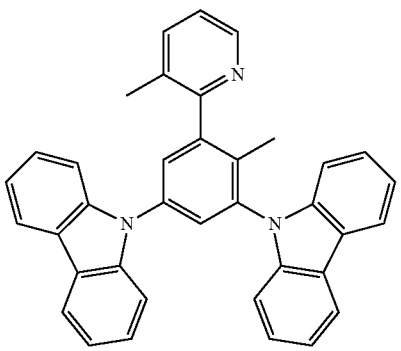
2-20
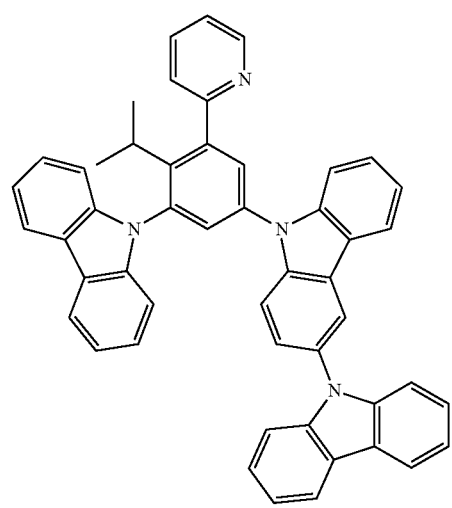
3-2
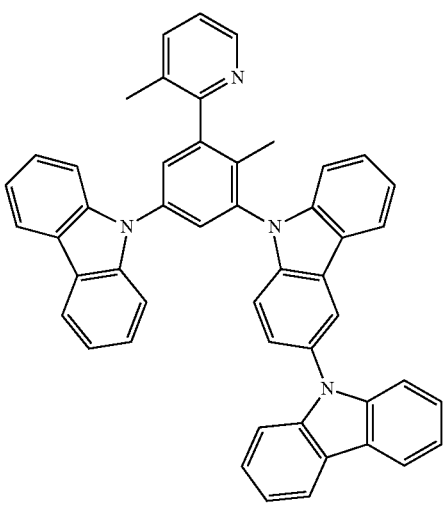

3-3
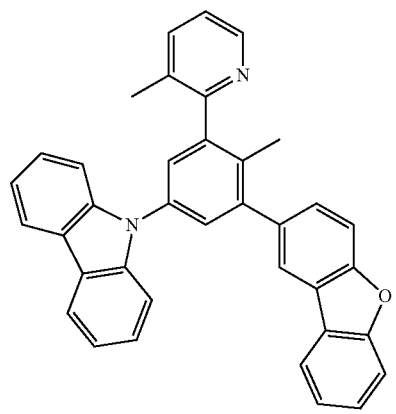
3-4
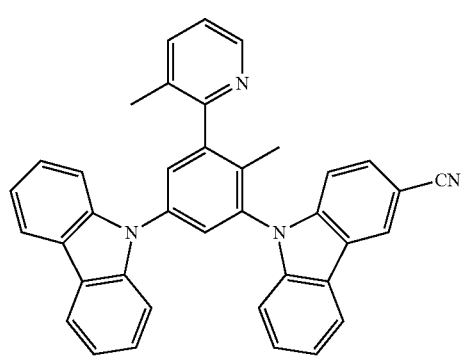
3-5
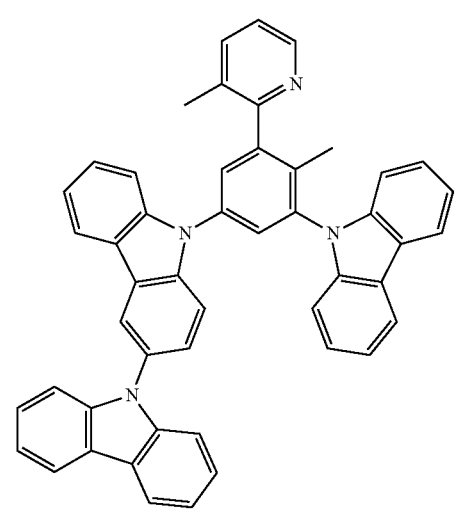
3-6
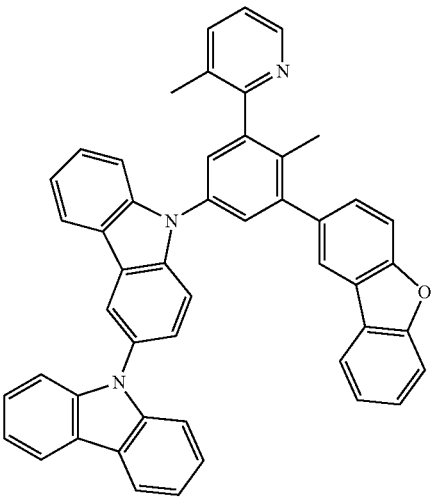
3-7
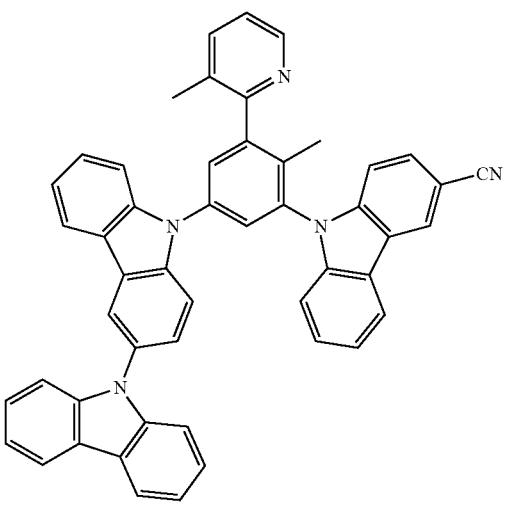
3-8
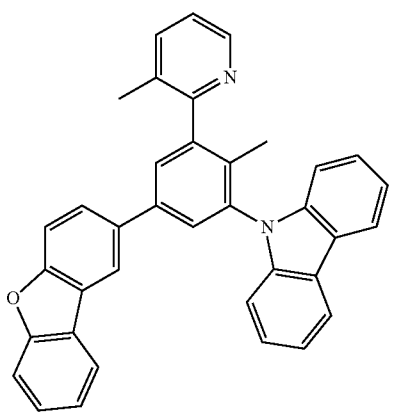

3-9
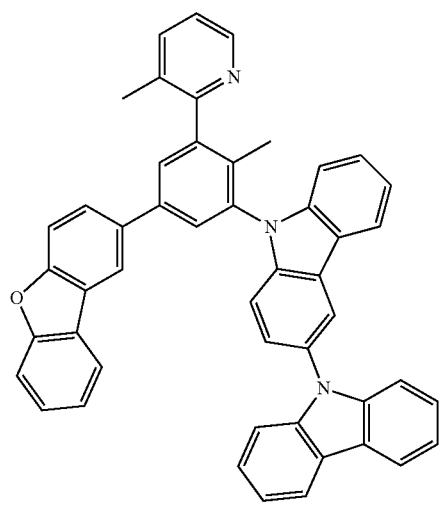
3-10
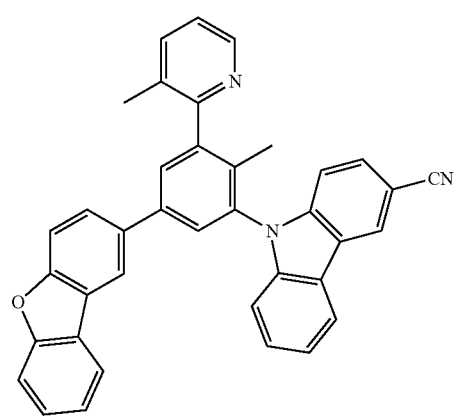
3-11
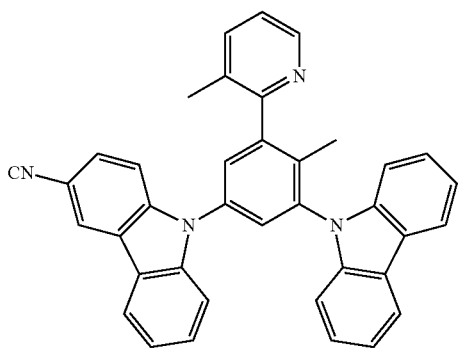
3-12
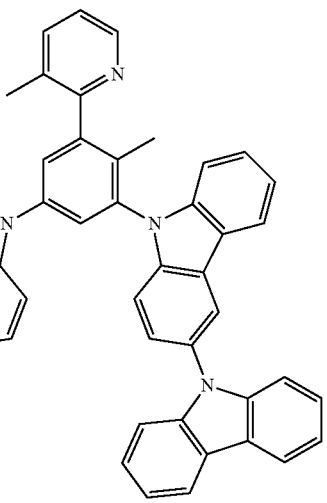
3-13
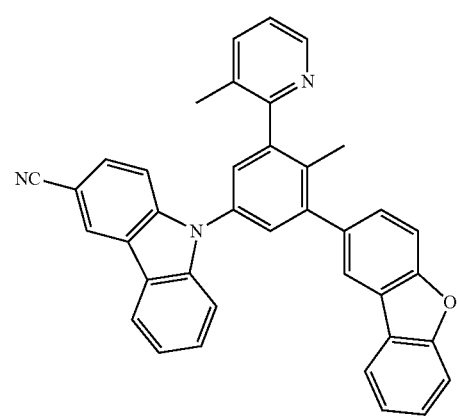
3-14
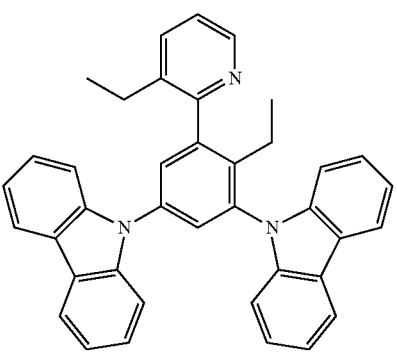

-continued
3-15
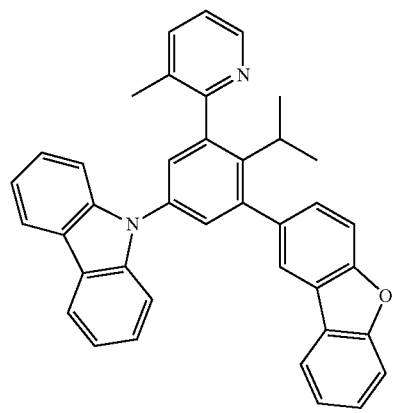
3-16
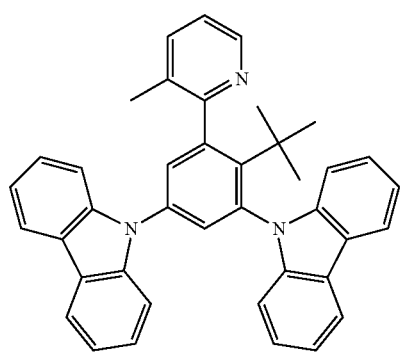
3-17
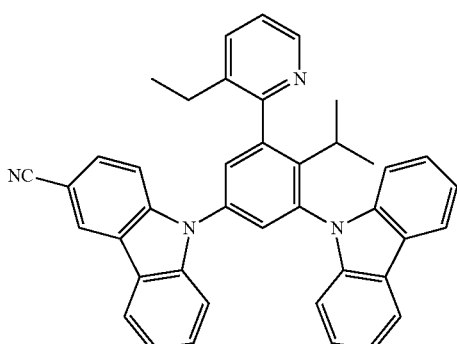
3-18
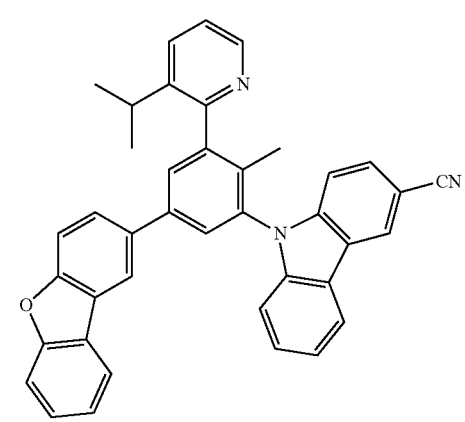
-continued
3-19
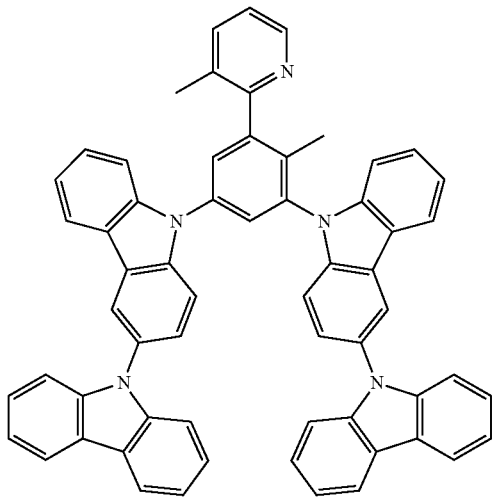
4-1
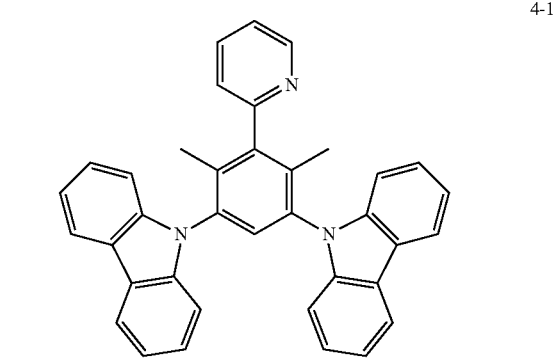
4-2
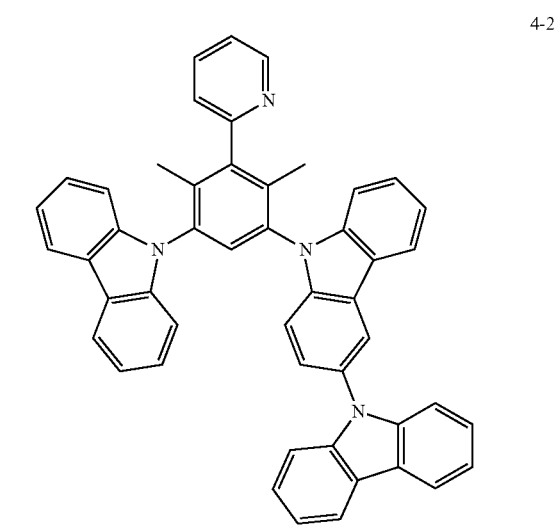

4-3
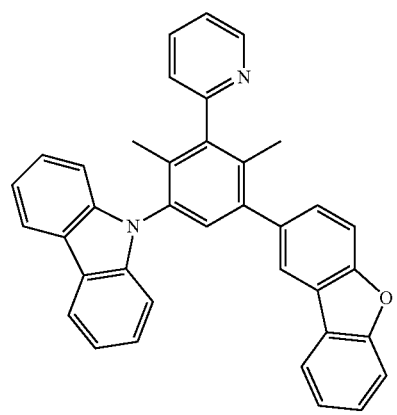
4-4
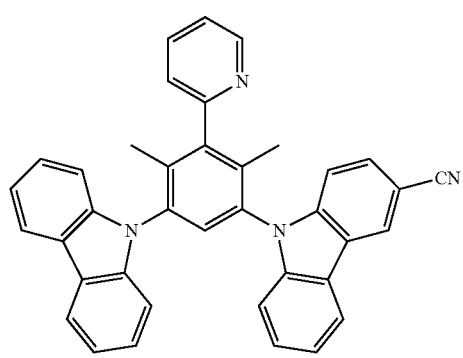
4-5
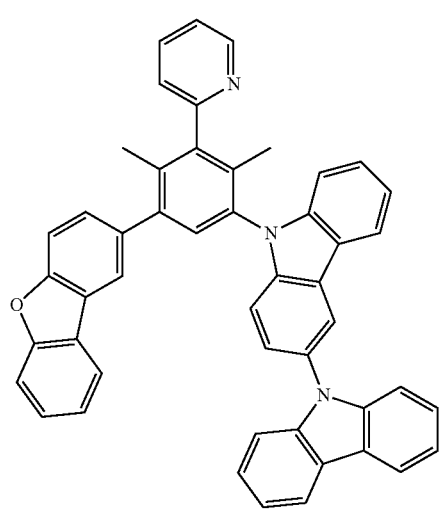
4-6
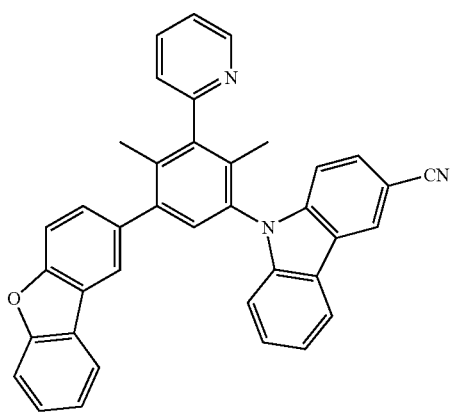
4-7
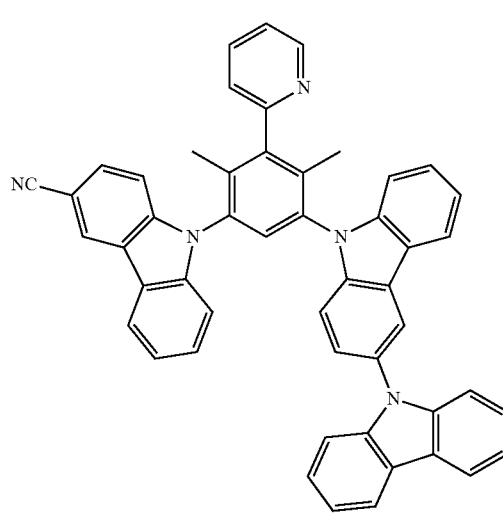
4-8
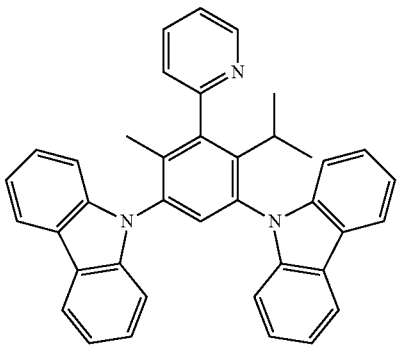

4-9
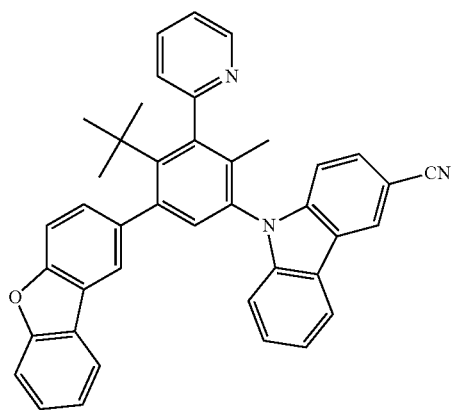
4-10
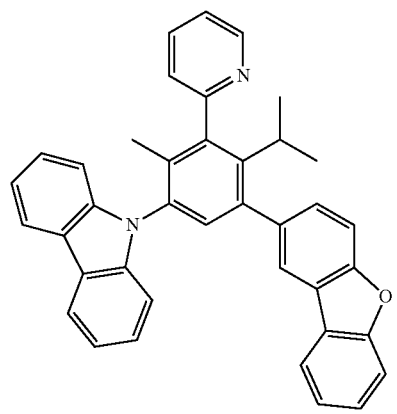
4-11
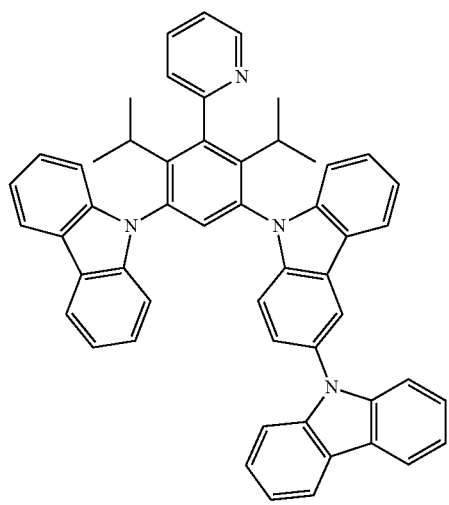
4-12
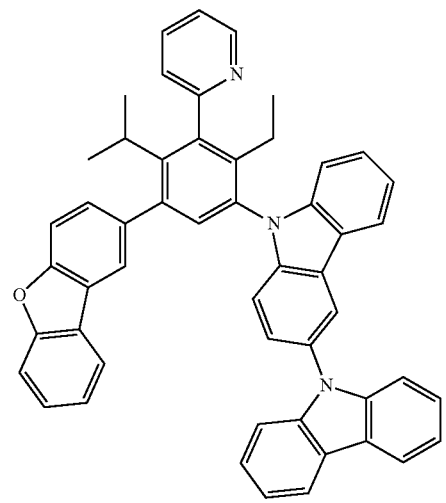
4-13
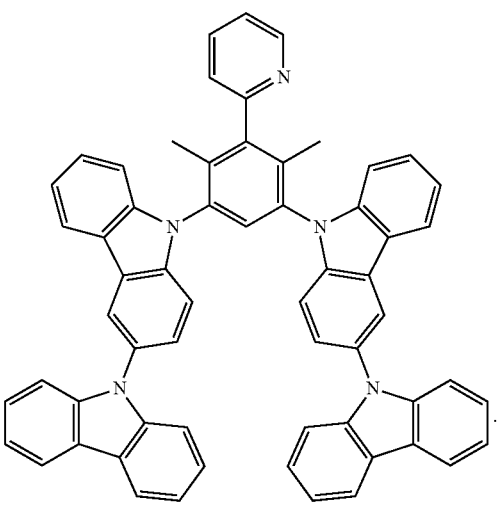
14. The organic light emitting display device according to claim 10, wherein the first dopant is:
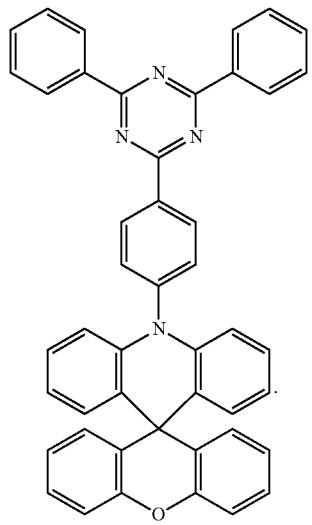 [SMILES: c1ccc(-c2nc(-c3ccccc3)nc(-c3ccc(N4c5ccccc5C5(c6ccccc6Oc6ccccc65)c5ccccc54)cc3)n2)cc1]

15. The organic light emitting diode according to claim 2, wherein each of D1 and D2 is selected from the group consisting of substituted or non-substituted carbazolyl, and non-substituted dibenzofuranyl, and a substituent in the substituted carbazolyl, if present, is a carbazole group or a cyano group.

16. The organic light emitting display device according to claim 11, wherein each of D1 and D2 is selected from the group consisting of substituted or non-substituted carbazolyl, and non-substituted dibenzofuranyl, and a substituent in the substituted carbazolyl, if present, is a carbazole group or a cyano group.

* * * * *